United States Patent [19]

White et al.

[11] Patent Number: 5,129,262

[45] Date of Patent: Jul. 14, 1992

[54] PLATE-MODE ULTRASONIC SENSOR

[75] Inventors: Richard M. White, Berkeley; Stuart W. Wenzel, Kensington, both of Calif.

[73] Assignee: Regents of the University of California, San Francisco, Calif.

[21] Appl. No.: 467,412

[22] Filed: Jan. 18, 1990

Related U.S. Application Data

[63] Continuation of Ser. No. 162,193, Feb. 29, 1988, abandoned.

[51] Int. Cl.$^5$ .............................................. G01N 9/24
[52] U.S. Cl. .................... 73/599; 310/313 R
[58] Field of Search ................ 73/599, 602; 333/147, 333/149; 310/313 R, 313 B, 313 A

[56] References Cited

U.S. PATENT DOCUMENTS 4,404,852  9/1983  Goto ..................................... 73/599
4,598,224  7/1986  Ballato ............................. 310/313 R

OTHER PUBLICATIONS

Ultrasonic Transducers by J. de Klerk, Ultrasonics, vol. 9, No. 1, Jan. 1971, pp. 35–48.

Primary Examiner—Hezron E. Williams
Assistant Examiner—Louis M. Arana
Attorney, Agent, or Firm—Owen, Wickersham & Erickson

[57] ABSTRACT

An ultrasonic sensor which has a thin planar sheet of material forming a Lamb wave propagation medium, the sheet having a thickness which is no greater than about twenty microns. The sensor also includes a Lamb wave generator for generating Lamb waves in the propagation medium and an output device for producing an electrical signal representative of the propagation characteristics of the Lamb waves propagating along the propagation medium. A measuring device is included in the sensor to measure selected characteristics of the output electrical signal. The propagation medium has some physical characteristics that are determined by the value of a measurand acting on the medium and the determined physical characteristics determine the propagation characteristics of the Lamb waves which are propagated along the medium. When the sensor is acted on by a measurand to determine the physical characteristics of the propagation medium, the characteristics of the electrical signal are also determined. The measuring device measures the electrical signal and provides an indication of the measurand value. Several sensing arrangements are also disclosed as well as methods for making the planar propagation medium.

39 Claims, 13 Drawing Sheets

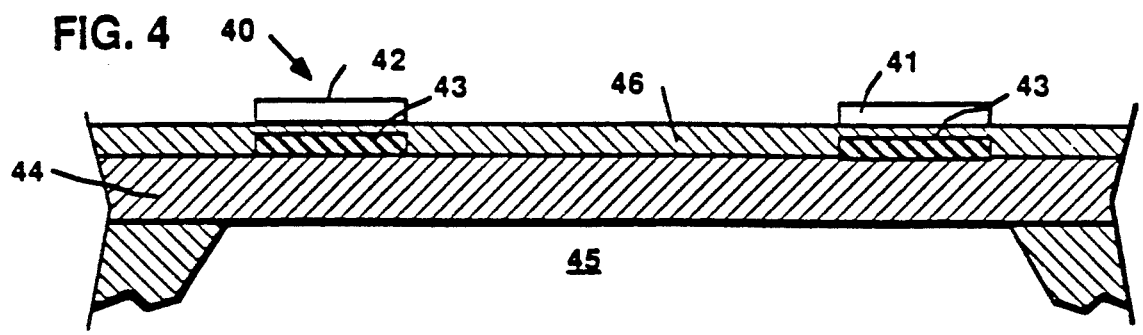
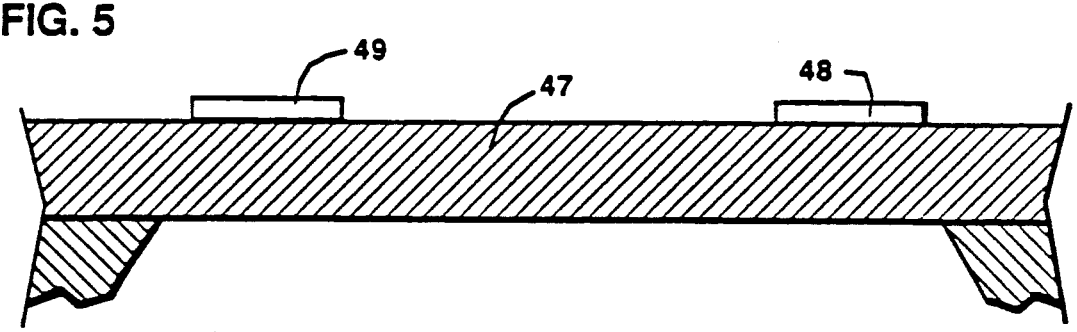
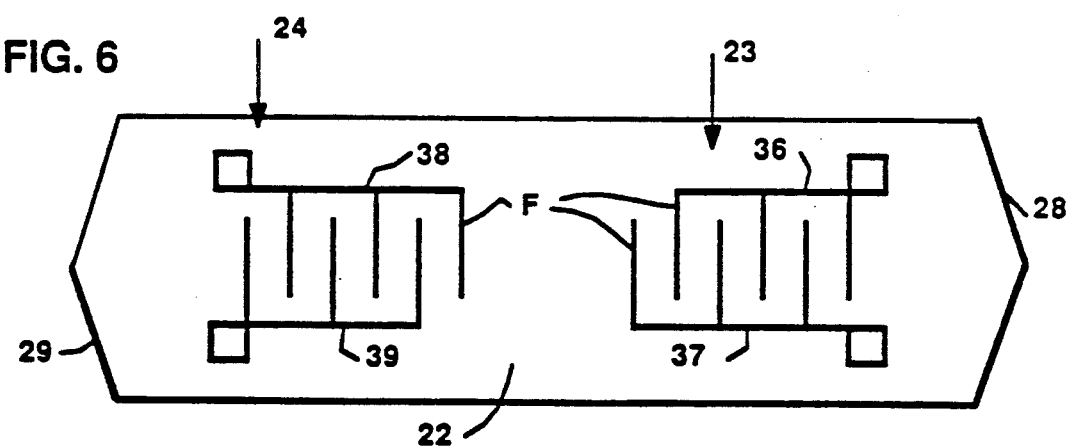
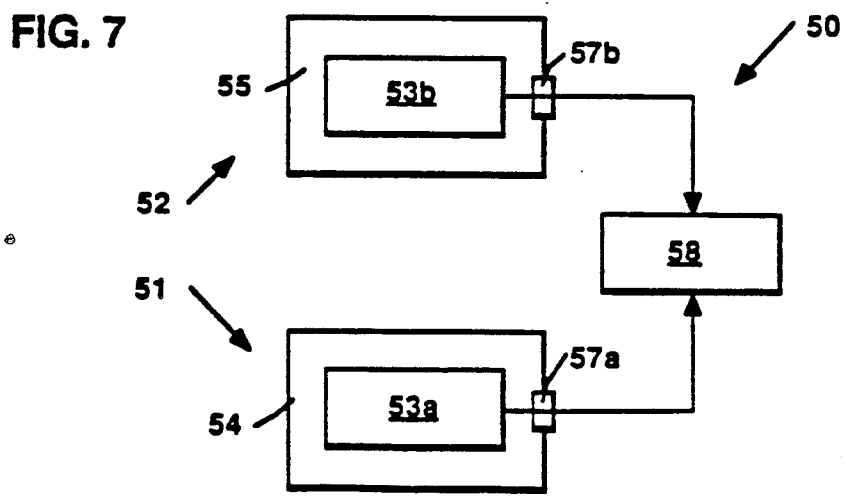

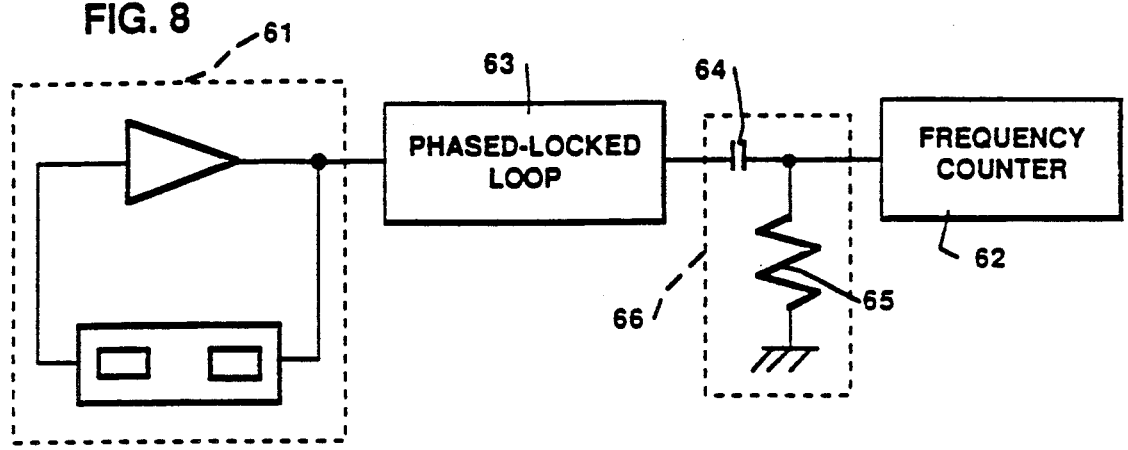
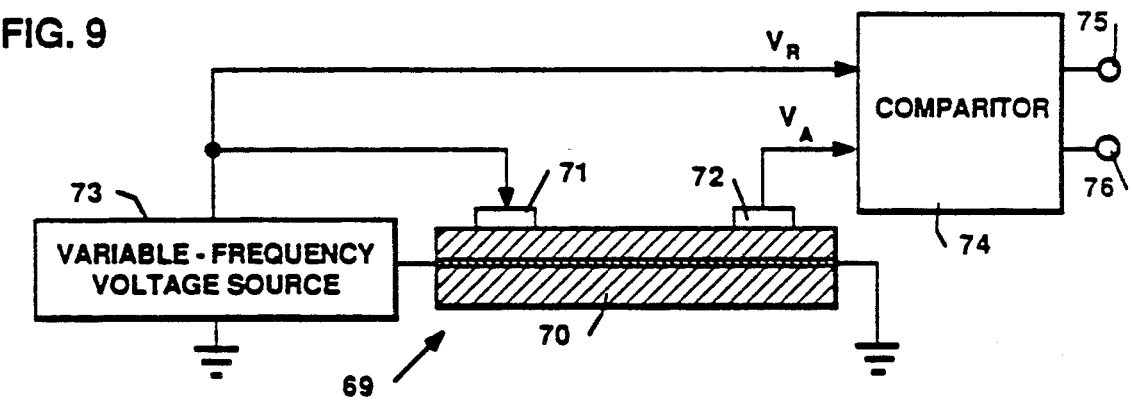
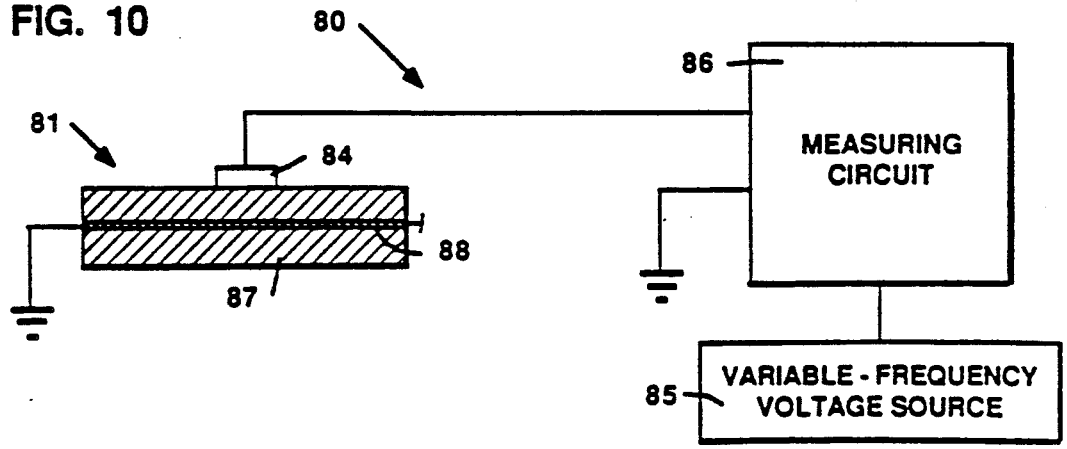

PLATE-MODE ULTRASONIC SENSOR

This is a continuation of co-pending application Ser. No. 07/162,193 filed on Feb. 29, 1988, now abandoned.

This invention relates to ultrasonic sensors, and particularly to ultrasonic sensing devices which utilize Lamb waves to sense changes in a measurand or to determine the value of a measurand.

The invention also relates to method and apparatus for generating, receiving, and processing Lamb waves and to method and apparatus utilizing Lamb waves for sensing and quantifying phenomena hitherto either not sensed or not quantified with sufficient accuracy.

BACKGROUND OF THE INVENTION

The phenomenon responsible for the operation of ultrasonic oscillator sensors is elastic wave propagation along a medium whose characteristics can be altered by a measurand. Where the characteristics of the waves propagating along the medium are dependent upon the characteristics of the propagation medium the wave characteristics can be monitored or measured provide an indication of the measurand value.

Many sensing applications have been found for Rayleigh or surface acoustic waves (SAW's). However, SAW's can only propagate through a semi-infinite medium, that is, a medium having a thickness which is many times their wavelength The propagation medium used by SAW sensors is commonly a piezoelectric substrate or a piezoelectric-coated substrate, the piezoelectric material cooperating with transducing electrode structures to generate and receive the SAW's.

SAW devices are shown, for example, in Dias and Karrer U.S. Pat. No. 3,878,474, in which a SAW oscillator is employed as a force-sensing device, and in Schulz and Holland U.S. Pat. No. 3,786,373, which discloses a temperature-compensated SAW resonator device which is not specifically designed for use as a sensing element The latter patent includes a double substrate arrangement in which interdigital electrode arrays are disposed upon a substrate which may be deposited upon the surface of a non-piezoelectric layer which, in turn, is placed upon the surface of a piezoelectric substrate, giving a propagation medium that is thick relative to the wavelength of the SAW's.

Willingham et al. U.S Pat. No. 3,965,444 shows another temperature-compensated SAW device, having a $SiO_2$ film layer on a substrate of piezoelectric material, and Okamoto, et al. U.S. Pat. No. 4,480,209 shows a SAW device with a silicon substrate that is thick compared to the wavelength of the SAW's, together with a zinc oxide piezoelectric layer deposited thereon.

Inoue et al. U.S. Pat. No. 4,456,850 shows a high-frequency piezoelectric composite "thin-film" resonator in a fundamental thickness-extensional vibration mode. It is said to have good temperature stability and resonance response Inoue uses "thin films" having particular resonant frequency characteristics, but only as part of a thick sandwiched structure having the piezoelectric materials to achieve the temperature stability.

A number of problems arise in SAW sensing devices due to SAW characteristics or to the characteristics of the medium required for SAW propagation. One such problem is that it is difficult to operate SAW sensors while they are immersed in most liquids, a problem rendering them inappropriate for many biological and chemical sensing applications. The reason is that when SAW devices are immersed, the SAW velocity is higher than the velocity of sound waves through the liquid; a large amount of the SAW energy is therefore radiated into the liquid, and the wave is attenuated as it travels along the propagation medium.

Another problem with SAW sensors is that the thickness of the SAW propagation medium makes such devices inappropriate for certain sensor applications. Furthermore, SAW sensor devices lack the degree of sensitivity required for many possible sensor applications.

A voltage sensor which utilizes a Lamb wave delay line oscillator has been proposed by K. Toda and K. Mizutoni in the Journal of the Acoustical Society of America, Vol. 74(3), pages 677–79, 1983. The delay line uses a piezoelectric ceramic plate with a third electrode that changes the acoustic path length of the piezoelectric plate in response to an applied voltage. Although the ceramic plate is capable of supporting Lamb waves, it is still a relatively thick medium, having a thickness of 180 micrometers. This ceramic plate thickness is required for mechanical stability. However, this propagation medium thickness decreases the sensitivity of the voltage sensor and increases the velocity of Lamb waves which propagate therethrough. Also the thickness required of the Toda/Mizutomi propagation medium results in a device that is ill suited for many potential sensing applications.

A metallic Lamb-wave structure has been proposed by Uozumi et al. for use in measuring the elastic properties of thin metallic films as described in Applied Physics Letters, Vol. 43(10), pages 917–19, 1983. The Uozumi et al. Lamb-wave structure teaches a lamb wave propagation medium that includes a metal base material on which is formed a piezoelectric film. The metallic base layer is formed by plating copper, to a thickness of three microns, onto an evaporated copper film on a disposable substrate. The piezoelectric film is deposited on this base material and transducer electrodes are deposited on the piezoelectric film to form a delay line structure.

The structure shown by Uozumi et al. is difficult to fabricate and the resulting propagation medium is wrinkled out of its plane due to the compressive stresses developed on the metallic base layer during piezoelectric film deposition that deform the metallic layer substantially. This is in contrast to the Lamb-wave sensor of the present invention, which has a propagation medium that is planar in form, even on its small scale Also, propagation media pursuant to the teachings of Uozumi et al. are inappropriate for many possible sensor applications due to the properties of the metallic base material.

It is therefore an object of the invention to provide an ultrasonic sensor which exhibits high sensitivity.

Another object is to provide an ultrasonic sensor having a sensitivity at least an order of magnitude greater than the best SAW device currently available.

Another object is to provide an ultrasonic sensor having a small heat capacity so that it can respond rapidly to heating.

A further object of the invention is to provide an ultrasonic sensor device that can operate fully satisfactorily while immersed in fluids of most types.

These and other objects, advantages, and features of the invention will be apparent from the following summary of the invention and description of preferred embodiments, considered along with the accompanying drawings.

SUMMARY OF THE INVENTION

The invention marks a departure from the use of SAW's or Rayleigh waves in ultrasonic sensors and employs instead Lamb waves, which are also known as plate-mode waves. Lamb waves can propagate only through a material of finite thickness. In contrast to SAW's, which require a propagation medium having a thickness on the order of hundreds of times the wavelength of the SAW propagating therethrough, Lamb waves require a propagation medium which is at most only several wavelengths thick.

The invention also marks a departure from the previously proposed Lamb wave voltage sensor, which uses a relative thick but finite medium and relies only on a change in acoustic path length to detect a measurand. In contrast, the sensor according to the invention uses a very thin propagation medium which can be affected by a measurand in several different ways to produce a sensor output. Also, the sensor pursuant to this invention is capable of taking advantage of special Lamb wave characteristics that arise in plates whose thickness is comparable with or small as compared to the wavelength of the wave.

The invention includes a thin propagation medium capable of supporting Lamb waves, generating means for generating Lamb waves along the propagation medium, conversion means for converting the Lamb waves into electrical signals representative of the waves, and measuring means for measuring certain characteristics of the electrical signals which represent the Lamb waves propagating along the medium.

The wave generating means cause Lamb waves to propagate along the propagation medium, the medium also having material characteristics which can be altered by a measurand. Changes in the propagation medium characteristics, in turn, cause changes in the wave characteristics of the Lamb waves propagating along the medium. The Lamb wave characteristics are measured or monitored by the measuring means to detect changes in, or to determine the value of, a measurand.

The propagation medium comprises a very thin planar sheet of material which is capable of supporting Lamb wave propagation, and is preferably much thinner than the wavelength of the particular Lamb waves. For example, where the wavelength of the Lamb waves is on the order of 100 microns, the propagation medium is preferably approximately only a few microns thick or no greater than twenty microns. The propagation medium of a sensor according to this invention may have a thickness up to about two times the wavelength of the waves to be propagated through the medium. However, lesser thicknesses are readily obtainable and may be required to provide desired sensor characteristics for a particular application or to take advantage of special Lamb wave characteristics that arise in very thin plates.

The propagation medium may also be referred to as an acoustically-thin plate or a membrane Strictly speaking, it is neither a "plate" nor a "membrane" as those terms are usually defined in the mechanical engineering literature. Unlike such plates, the present plate is so thin that its elastic response to deformation can be influenced by in-plane tension that develops during the initial fabrication process. Also, since flexural Lamb waves can propagate on these structures, they are unlike membranes, which are formally regarded as being infinitely flexible. However, in spite of these formal differences, the terms "propagation medium", "plate", and "membrane" will be defined, for the purposes of this specification, and unless otherwise specified, as any structure capable of supporting Lamb wave propagation. Also, the term "Lamb waves" will be defined, for the purposes of this specification, as any elastic wave that propagates in a finite medium regardless of in-plane tension or lack of such tension in the propagation medium.

Since the propagation medium thicknesses are generally in the order of several microns, semiconductor microfabrication materials and techniques are preferably employed in the construction of the membrane. For example, in a preferred form, the membrane is formed on a silicon wafer and comprises a layer of silicon nitride, a layer of aluminum or other conducting material, and a layer of piezoelectric zinc oxide. A portion of the silicon beneath the silicon nitride layer is etched away to leave a thin membrane, supported along at least a portion of its periphery by the remaining silicon wafer.

The present sensor uses a transducer structure coupled to the propagation medium to generate both symmetrical and antisymmetrical mode Lamb waves in the medium. In one form, the transducer electrodes differentially deform a piezoelectric material that forms a layer of the propagation medium to produce a mechanical wave motion in the medium. In another form, the transducer electrodes can produce a sufficient electric field intensity to produce Lamb waves in the propagation medium without the need for a piezoelectric material.

In one form, the Lamb-wave sensor includes a delay line having a launching transducer and a receiving transducer, each coupled to the propagation medium. The launching transducer converts an electrical signal into a mechanical motion in the propagation medium to generate Lamb waves in the medium. The receiving transducer receives the Lamb waves and produces an electrical signal representative of the mechanical Lamb wave motion along the propagation medium or membrane.

The delay line form may also include a feedback path leading from the receiving transducer back to the launching transducer, having a feedback amplifier, for amplifying the signal produced by the receiving transducer. When sufficient gain is provided by the feedback amplifier, the device forms a feedback oscillator that will oscillate at the frequency of the Lamb waves propagating along the propagation medium.

Also, since semiconductor microfabrication materials and techniques can be employed in producing the membrane, the amplifier can be formed integrally with the propagation medium on a common substrate in, or as a part of, an integrated circuit chip.

In the feedback-oscillator embodiment of the Lamb-wave sensor, the measuring means may be a frequency counter which provides a reading of the oscillation frequency. As a measurand changes the propagation characteristics of the propagation medium or membrane, the oscillation frequency changes. Thus, the oscillation frequency indicates the change in and the value of the particular measurand.

In another form, the delay line is operated as a passive device rather than as an oscillator. In this form, a voltage source supplies the launching transducer, and the receiving transducer is connected to a suitable measuring instrument to determine the relationship between the output and the input signals of the delay line.

Where the delay line structure is operated as a passive device, the measuring means includes a signal amplitude measuring means for measuring the insertion loss of the delay line. This loss depends on the transducer efficiency and the amplitude loss of the Lamb wave as it propagates along the propagation medium. The measuring means may also include means for measuring the phase shift of the Lamb wave as it travels along the propagation medium.

The Lamb-wave sensor of the invention may also be operated as a active or passive one-port device, in which case a single transducer is coupled to the propagation medium. In the passive form, the single transducer is connected to a measuring circuit that determines its input impedance as a function of frequency. In the active one-port embodiment, the transducer is connected into an oscillator circuit where it is the frequency-determining element.

The Lamb waves in this invention have a velocity between 100 and 10,000 (meters per second), as compared with the velocity of 3,000 to 6,000 m/s for SAW's. Also, whereas the SAW's have only a single mode of wave propagation, this mode being non-dispersive, and whereas the Toda voltage sensor couples only to symmetric Lamb wave modes, the Lamb waves of the present sensor have many modes of propagation, some of which are or may be dispersive or antisymmetrical.

An important feature of the present sensor is that the wave velocity of the zeroth-order antisymmetrical Lamb waves in the present propagation medium, is lower than the velocity of sound through most fluids. Therefore, in this mode of propagation, the Lamb waves propagating along the propagation medium or membrane cannot radiate energy into a surrounding fluids. Thus, the sensor may be operated while immersed in fluids. This is in contrast to SAW sensors, in which SAW velocities are higher than the velocity of sound through most fluids, a characteristic which renders typical SAW sensors inappropriate for operation while immersed in fluids.

The Lamb-wave sensor of this invention may operate in a frequency range of approximately 1 to 200 MHz. By contrast, the SAW sensors operate in a frequency range of 10 to 2,000 MHz. The lower-frequency operation of sensors pursuant to this invention is much more convenient in terms of the costs of associated electronic equipment, such as frequency counters and feedback amplifiers, for example.

The novel sensor of this invention can be used in many different sensor applications. For example, it may be used as a microphone, a biosensor, a chemical vapor or gas detector, an accelerometer, a manometer or other pressure-measuring device, a densitometer, a radiometer, or a thermometer.

As an example, consider the use of the device as a manometer to determine gas pressure. When exposed to a steady pressure on both sides of the propagation medium, the sensor of this invention produces a constant-frequency output having a typical value around five megahertz. When the pressure on one side of the propagation medium rises, the output frequency rises monotonically In one experimental sensor tested, the frequency shifted 0.65 Hz per microbar. This compares very favorably with a prior-art SAW pressure sensor whose output may also be a changing frequency, for the device of the present invention is sixteen times more sensitive, while operating at a frequency about twenty-three times lower than that of the SAW device.

Also, where the sensor forms an oscillator, the oscillator frequency can be stable to better than one part in one million. Thus, in the pressure-sensor example, the device can detect pressure changes as small as a few microbars (millionths of atmospheric pressure).

The invention can also be configured to measure a pressure applied to both sides of the propagation medium or membrane. Pressure applied to the membrane in this fashion will affect the loading of the propagating Lamb wave and may have both dissipative and velocity effects on the wave. However, as mentioned earlier, where the phase velocity of the Lamb wave in the membrane is smaller than the sound wave velocity in the fluid being measured, no wave energy will be radiated to the fluid, and there will be no dissipative effect. The requisite low antisymmetric wave velocity can be achieved by choosing an appropriately low ratio of membrane thickness to wavelength and a low value of in-plane tension.

The dimensions of the sensor can be adjusted so that the center frequency of its antisymmetric mode lies anywhere from 1 MHz to as much as 100 MHz. The range of operating pressure for the device can likewise be adjusted by scaling the device dimensions.

Where the sensor is employed as a microphone, the membrane produces an output that varies about a fixed carrier frequency in response to an incident sound wave. Specific applications include using the device as a sound pickup in a gas or liquid, or through solid contact for vibration monitoring.

The Lamb-wave device can also be employed in biological sensing. For example, the membrane can be pre-coated with antibody molecules, so that the frequency of the device changes upon immersion in a liquid that contains the corresponding antigen. Antigen-antibody attachment at the surface of the propagation medium acts to alter the wave velocity causing the oscillation frequency to change in the delay line oscillator form. Also, the membrane may be made of a porous and permeable material, allowing the coating of a greater surface area and also allowing the antigen-containing liquid to be flowed through the membrane, in order to speed up the antigen-antibody attachment. Other biological interactions may also be sensed, and additional applications include immunoassay, clinical laboratory testing, in vivo biomedical monitoring, and biomedical research.

The new sensor can also be employed in chemical sensing applications. For example, when the device absorbs vapors or gases from the atmosphere in a film deposited on the membrane, the output frequency changes. Simulations indicate that the device is at least an order of magnitude more sensitive than a SAW vapor sensor operating at the same wavelength, for example at 141 micrometers.

Despite the thinness of the propagation medium or membrane, a sorptive film can be spun directly onto a freely suspended membrane in a functioning device. A heating element can be placed on the membrane surface opposite or beneath the sorptive film, and the temperature of the membrane can be cycled repeatedly in a known fashion, such as linearly as a function of time. The oscillation frequency can be measured during each cycle of temperature increase. Molecules or atoms sorbed in the film will be desorbed and leave the film at different characteristic temperatures. The temperature at which the oscillation frequency changes markedly, indicating desorption of molecules from the film, can provide an indication of the type of molecule that was present. This application of thermal desorption spectroscopy, with the Lamb-wave sensor, can increase the ability of the sensor to detect vapors and gases selectively, and the sensor can also be used in research on the sorption of molecules or atoms. Use of the device as a test bed for research on chemical reactions is also attractive. Applications include process control, pollution monitoring, personnel dosimetry, and other chemistry research.

In addition to thermal desorption spectroscopy, some suitable membrane materials are optically transparent, enabling the device to incorporate optical beams for photothermal, photoacoustical, and optical desorption spectroscopy. The sensor may be used as a dosimeter in circumstances where particles, such as ions or fission fragments, pass through or are captured in the propagation medium, altering its propagation characteristics. For example, mass loading from captured particles may affect the propagation medium or membrane stiffness. To increase the effect of such particles, the membrane may have a suitable film which is strongly affected by the particles of interest.

In addition to the mechanical application as a pressure sensor described above, the new sensor is also sensitive to other characteristics of a medium in which it is immersed. For example, the density of the fluid medium surrounding the membrane affects the characteristics of the Lamb waves that propagate through the medium. Thus, it is feasible to monitor fluid density, as well as other properties, to high precision, such as one part in one million, or better. Applications include process control, transportation, and metrology.

Since absorption of radiant energy causes the membrane of the present sensor to be heated, thereby changing the Lamb wave characteristics, optical and thermal applications are also possible Functioning as a radiometer, the device can detect the presence of radiant sources whose temperatures are only 0.01 degree Celsius above ambient. Response to steady temperature is even more sensitive. Applications include security systems, sensing fault-produced heating, wide-range radiometry, and temperature sensing.

In some biological and chemical sensing applications, devices pursuant to the invention can have inexpensive disposable sensor elements that are inserted into a small instrumented holder for readout. The sensor elements in this form can comprise a propagation medium and transducer structure that can be inserted in a holder that includes all auxiliary electronic components needed to provide a sensor readout.

Unlike most other sensors, the present sensor may conveniently operate at several alternative frequencies that depend differently upon the influence of different measurands. By successively selecting broadly the operating frequency band of the amplifier in the delay line oscillator form, several oscillation frequencies may be measured with a single sensor and from them, the sensor can determine the values of several different measurands.

The new sensor can also be constructed for simultaneous multi-frequency operation. In the delay line form, several band-pass filter and amplifier series combinations can be added in parallel, to form the feedback path. Each filter may pass a different frequency to its associated amplifier and produce oscillation, and each separate frequency can be measured with a frequency counter. In this way, a single propagation medium may be used to sense several measurands.

The propagation medium or membrane can also be constructed for shear horizontal propagation of Lamb waves. Such Lamb waves along the propagation medium are particularly sensitive to the viscosity of a surrounding fluid.

Also, an isotropic propagation medium or membrane material enables multi-directional operation, with the generated Lamb waves propagating in different directions at an angle to each other and at possibly different frequencies. In these embodiments, a set of transducers is used for each propagation direction, each set having a launching and receiving transducer. Such a sensor may efficiently utilize the area of the membrane to provide simultaneous indication of several measurands.

BRIEF DESCRIPTION OF THE DRAWINGS

FIG. 4 is a schematic cross-sectional view a sensor having only a partial ground plane.

FIG. 5 is a schematic cross-sectional view a membrane that consists entirely of a piezoelectric material.

FIG. 6 is a somewhat schematic top plan view of the sensor shown in FIG. 1, showing the transducer arrangement.

FIG. 7 is a schematic representation of a selective Lamb wave sensor that includes a reference oscillator.

FIG. 8 is a schematic representation of a Lamb-wave sensor having an output that is compensated to exclude slowly-varying phenomena.

FIG. 9 is a schematic cross-sectional view of an alternative embodiment of a sensor according to the invention.

FIG. 10 is a schematic cross-sectional view of a passive one-port sensor embodying the principles of the invention, drawn to an exaggerated vertical scale.

DESCRIPTION OF THE PREFERRED EMBODIMENTS

Figure 1:
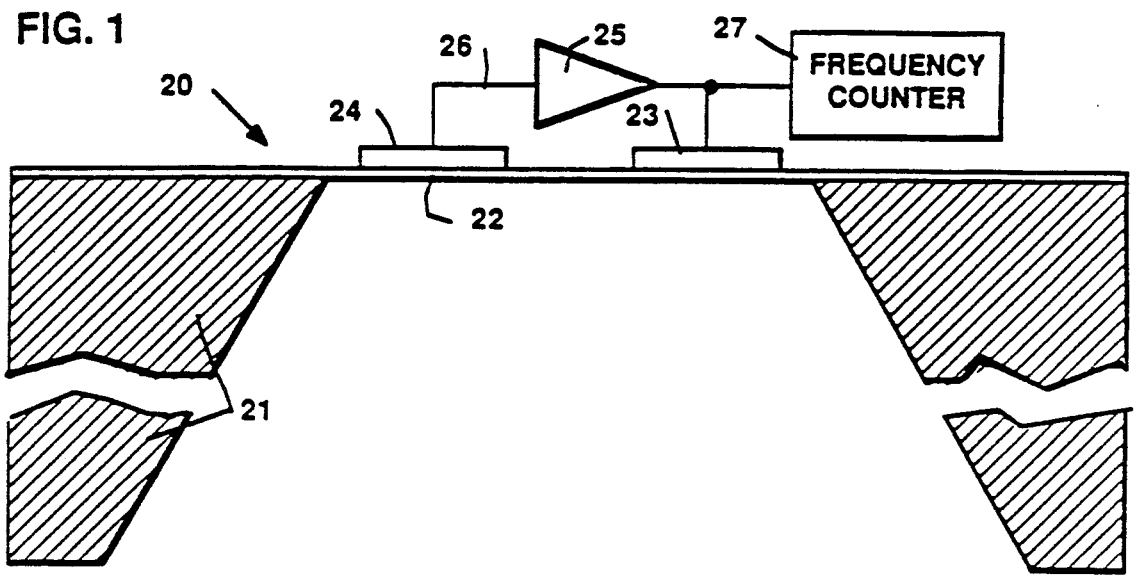
FIG. 1 is a greatly enlarged schematic cross-sectional view of a Lamb wave sensor embodying the principles of the invention, drawn to an exaggerated vertical scale.

FIG. 1 illustrates one form of a Lamb wave ultrasonic sensor 20 embodying the principles of the invention. The sensor 20 includes a substrate 21 that supports a propagation medium or membrane 22. A launching transducer 23 and a receiving transducer 24 are located on the propagation medium at spaced-apart locations. Separated from the propagation medium 22, a feedback amplifier 25 is connected in a feedback path 26 between the receiving and launching transducers, and a frequency counter 27 is connected to the output of the feedback amplifier 25.

Figure 2:
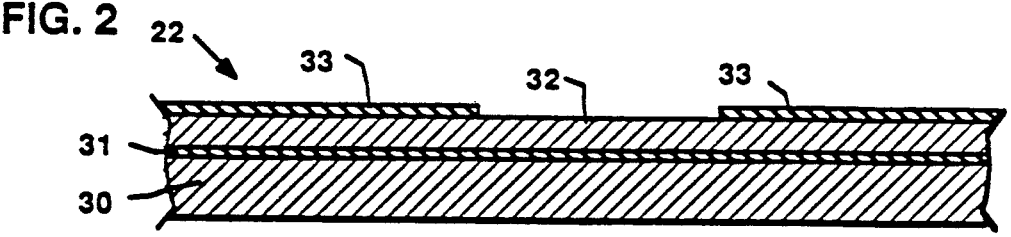
FIG. 2 is a further enlarged view of a portion of the membrane of FIG. 1.

A preferred form of the propagation medium or membrane 22 is shown in detail in FIG. 2. The membrane 22 is a planar sheet of material comprising a film or base layer 30 of nonconductive or semiconductive base material, a film 31 of conductive material, and a thin film 32 of piezoelectric material. A layer 33 of conductive material representing a portion of a transducer structure is also shown deposited on the upper surface of the membrane 22. The propagation medium 22 shown in FIG. 2 may be formed, pursuant to the invention, having an inherent tensile stress, as may the other propagation medium forms of the invention. This inherent tensile stress may be used to advantage in sensing applications and also helps in maintaining the true planar form of the propagation medium.

The base layer 30 may be made of silicon nitride having a thickness of approximately 2.0 microns. The layers 31 and 33 may both be aluminum, each approximately 0.3 microns in thickness, the layer 31 forming a ground plane for the transducers and the material 33 forming the transducer electrodes. The piezoelectric layer 32 may preferably comprise zinc oxide having a thickness of approximately 0.7 microns.

Figure 3:
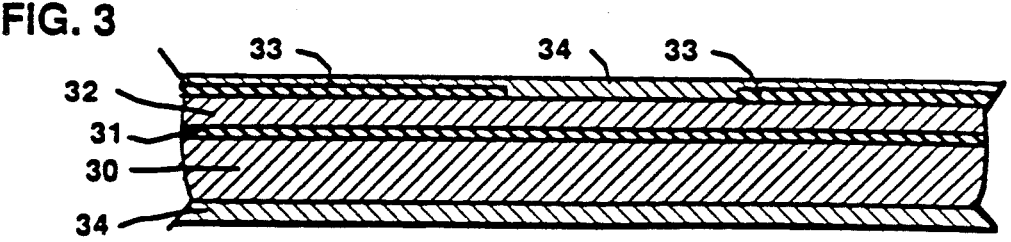
FIG. 3 is an enlarged view similar to FIG. 2, but showing a portion of a membrane that includes a protective coating.

As shown in FIG. 3, the propagation medium or membrane may include a protective coating 34. For example, the protective coating 34 may comprise a thin layer of polytetrafluoroethylene (Teflon) that prevents corrosion of electrodes when the sensor is immersed in liquids or is operated in corrosive environments. The protective coating 34 may alternatively be a thin silicone coating to prevent blood coagulation at the sensor's surface, when it is used for in vivo monitoring in the cardio-vascular system.

Another alternative propagation medium 40 is shown in FIG. 4. In this form of the sensor, there is no ground plane along at least a portion of the propagation medium between two transducer structures 41 and 42. Rather, a ground plane 43 is restricted to the area of the transducers 41 and 42. With this propagation medium 40, the electric fields generated by the piezoelectric material 46 can extend into a dielectric liquid 45 on the other side of the silicon nitride layer 44. Thus, the sensor employing this propagation medium 40 can respond to the dielectric and conducting properties of the liquid 45.

In FIG. 5 the propagation medium or membrane consists entirely of a piezoelectric film 47. Transducers 48 and 49, shown schematically, are coupled to the piezoelectric film 47 for generating both symmetrical and antisymmetrical Lamb wave modes. In this case the film 47 may be a piezoelectric polymer such as polyvinyl-fluoride.

FIG. 6 shows the preferred transducer structure in plan. Both the launching and the receiving transducers 23 and 24 respectively, are interdigital finger transducers deposited directly on the propagation medium 22. The launching transducer 23 comprises two electrodes 36 and 37, and the receiving transducer 24 comprises two electrodes 38 and 39.

In operation of the embodiment illustrated in FIGS. 1, 2, and 6, the Lamb waves are launched at the launching transducer 23, with the transducer electrodes 36 and 37 being drive differentially with respect to the ground plane 31. Thus, an alternating electrical field is created between each electrode finger F and the ground plane 31 across the piezoelectric layer 32. The piezoelectric layer 32 is deformed in response to the alternating field and generates a Lamb wave, which then propagates along the propagation medium 22. The wavelength of the Lamb wave so generated is approximately equal to period P of the electrode fingers or an odd integral fraction of P, such as P/3 or P/5, for example.

In order to generate antisymmetric mode Lamb waves in a propagation medium, some asymmetry is required. An asymmetrical membrane or propagation medium is one that does not have perfect symmetry with respect to an imaginary plane that is parallel to and equidistantly spaced from the two outer surfaces of the membrane From such an asymmetrical structure, both antisymmetric and symmetric mode Lamb waves may be generated.

In the membrane embodiments illustrated in FIGS. 2, 3, and 4, asymmetry is provided by the different thicknesses of the membrane constituent layers. In the membrane shown in FIG. 5, which has only a single layer 47 of piezoelectric material, asymmetry is provided by having no ground plane electrode. If a ground plane electrode is used in a single layer membrane, asymmetry may be provided by making the ground plane from a material having a different weight from the transducer electrode material, or by making the ground plane with a different thickness.

The Lamb waves launched at the transducer 23 propagate along the propagation medium or membrane 22 to the receiving transducer 24 and cause a deformation of the piezoelectric layer 32 at the receiving transducer 24. This wave-induce deformation of the piezoelectric layer 32 causes an electrical signal at the transducer 24, which is representative of the Lamb wave at that point.

Waves naturally launched by the transducer 23 in a direction away from the transducer 24 are prevented from interfering with sensor operation by angled ends 28 that reflect these unwanted waves, so that their wavefronts are no longer parallel to the electrode fingers of the transducers. Also, the Lamb waves that travel past the transducer 24 are reflected similarly at angled ends 29 to prevent their reflections from actuating the transducers. Alternatively, a dissipative absorptive material, such as a wax, may be placed on the membrane 22 beyond the transducers 23 and 24 to prevent wave reflections.

The signal received at the transducer 24 is fed back along the feedback path 26 to the amplifier 25, where the signal is amplified sufficiently to sustain oscillation. The amplified signal is then fed back to the launching transducer 23. The transducers 23 and 24, the propagation medium 22, and the feedback amplifier 25 thus form an oscillator that operates at the frequency of the Lamb waves travelling through the propagation medium 22. For a given Lamb wave mode, such as the zeroth-order antisymmetric mode, the frequency response of the amplifier gain determines at which of its possible frequencies the device will oscillate.

The frequency counter 27 is preferably connected to the feedback path 26 at the output of the amplifier 25, where the signal representing the Lamb wave is greatest. The frequency counter 27 includes a display (not shown) that provides a readout of the oscillation frequency.

The Lamb-wave sensor illustrated in FIG. 1, 2, and 6 senses a measurand that alters the characteristics of the material which makes up the propagation medium or membrane 22. These material characteristics include elastic stiffness, density, tension, thickness, length between the transducers, piezoelectric stiffening, and load mode, both reactive and dissipative. A change in the membrane material characteristics, in turn, affects characteristics of the Lamb waves propagating along the membrane 22. These latter characteristics are monitored to provide an indication of the measurand value.

The sensor embodiment illustrated in FIGS. 1, 2, and 6 can be used as a microphone, since an air-borne sound wave impinging on the membrane 22 will strain the membrane, causing the Lamb wave phase velocity to become time-varying and producing a modulation of the oscillator frequency. The microphone output will be a frequency-modulated voltage with information about the impinging sound wave carried in its sidebands.

Lamb wave phase velocity can be altered by physical changes that occur in a sensitive coating film on the membrane 2 when the coating interacts with chemical or biological species carried in a liquid. Also, zeroth-order antisymmetric Lamb waves have phase velocities low enough to permit their use while in contact with a fluid, without loss of wave energy to the fluid. Therefore, the sensor 20 can be operated while immersed in a fluid, an ability required for many chemical and biological sensing applications but difficult to achieve in SAW devices.

Since the Lamb-wave device responds to changes of membrane tension, surface loading, and changes in transducer dimensions, it is suited to a number of mechanical applications. A force applied to the membrane directly or to the substrate, strains the membrane and causes a change in oscillator frequency. Thus, the sensor could be employed as a scale for weighing very small masses. Also, since surface loading from the deposition of material on the membrane surface causes a response, the sensor can be employed as a deposition monitor for use in an evaporation or sputtering system, for example.

Response to gas or liquid pressure can be realized in two ways. If the propagation medium or membrane 22 is subjected to unequal pressures on its two sides, strain of the membrane will cause an oscillator frequency to change. If both sides of the membrane 22 are subject to the same pressure, the membrane tension will be constant, but loading of the propagating Lamb wave will depend upon the pressure, and so produce a sensor response.

Loading one or both sides of the membrane 22 with a fluid can cause large velocity changes and oscillator frequency shifts. Analysis shows that the magnitude of the change depends primarily upon the density of the fluid, the sound velocity in the fluid having a somewhat smaller effect. Thus, density and mass of the loading fluid may also be measured with the device illustrated in FIGS. 1–6.

Temperature has several effects on the wave propagation characteristics of the membrane or propagation medium 22. Temperature affects the elastic stiffness, tension, and density of the membrane 22, as well as the length of the membrane 22 between transducers. Thus, the device illustrated in FIGS. 1–6 can also be used to measure temperature with great sensitivity.

The sensitivity to temperature also makes it possible to use the sensor as a radiometer. As a radiometer, the incident radiation heats the membrane to cause the response Also, the response of the sensor as a radiometer can be increased by the addition on the membrane of a layer of black material, such as graphite, which strongly absorbs radiant energy.

The Lamb-wave sensor illustrated in FIGS. 1, 2, and 6 may be formed on a silicon wafer by depositing LPCVD silicon nitride uniformly over a wafer (not shown) and then etching away the silicon from beneath the nitride layer 30. The LPCVD silicon nitride can be deposited at 835° C. in a 5 to 1 gas ratio of dichlorosilane and ammonia, to obtain a low stress film suitable for fabricating membranes. Deposition time may be approximately 5 hours to obtain a 2 micron-thick film. Using a two-sided alignment technique, windows may be patterned in the backside nitride (not shown) by plasma etching Silicon may then be etched away, using the nitride as an etch mask, with ethylenediamine, pyrocatechol and water (EDPW) to leave a 2 micron-thick nitride membrane on the front side.

Following formation of the thin plate 30 of silicon nitride, zinc oxide piezoelectric material 32 may be sputtered onto a 0.30 micron-thick evaporated aluminum ground plane 31. The 0.7 microns of zinc oxide may be deposited by RF planar magnetron sputtering. Onto this layer 32 of zinc oxide, 0.30 microns of aluminum may be evaporated, using the marks generated during the two-sided alignment step to pattern interdigital transducers 23 and 24 centered on the membrane 22. For etching the aluminum, a solution of KOH, $K_3Fe(CN)_6$ and water (1 g:10 g:100 ml) may be used; this solution does not etch zinc oxide.

The feedback amplifier 25 used in the embodiment illustrated in FIG. 1 may comprise two cascaded LM733 differential video amplifiers. The device may be driven untuned, and an amplifier gain of approximately 40dB is necessary to sustain oscillation.

Alternatively, the feedback amplifier 25 may be formed integrally with the propagation medium on a common silicon wafer substrate. Semiconductor microfabrication techniques may allow other circuitry to be included on the substrate material, such as mixers, and frequency counters Drivers for sending signals off-chip for storage, interpretation, and display may also be formed on a substrate common with the propagation medium. A microprocessor and memory for converting frequencies into relevant physical, chemical, or biological parameters may also be included on the same base material.

The frequency can be measured with a frequency counter 27. A typical frequency counter is the Hewlett-Packard Universal Counter, model 5316A, which determines the frequency of an ac voltage from the number of polarity reversals that occur in an accurately known time interval. Such a counter can determine frequencies to a precision of 1Hz or better, and can output a binary indication of the frequency for transmission to auxiliary digital equipment for storage and processing.

For measuring the frequency of minimum insertion loss, RF pulses of 0.5–2 microsecond duration may be applied to one transducer 23, and the RF frequency can be tuned to maximize the received signal amplitude from the second transducer 24. The velocity of maximum transducer coupling is found by multiplying this frequency by the acoustic wavelength. Using the same apparatus, the group delay times could be measured, and hence group velocity.

As with other ultrasonic sensors, the Lamb-wave sensor of the invention encounters the problem of providing a response selective to the particular measurand of interest. The selective sensor embodiment 50 shown in FIG. 7, employs a reference device 51 and an active device 52, the active device 52 being exposed to all measurands that act on the sensor and the reference device 51 being exposed to all such measurands except the one of interest. The value of the measurand of interest is found by observing the difference in the active and reference device outputs.

The sensor 50 in FIG. 7 is a pressure sensor in an environment where temperature may be changing. The reference device 51 includes a Lamb-wave sensor element 53a enclosed in an inflexible enclosure 54. The active device 52 includes a Lamb-wave sensor element 53b, which is identical to the sensor element 53a, but in a flexible enclosure 55. Both enclosures 54 and 55 are filled with an inert filler gas 56. In the illustrated embodiment, the sensor elements 53a and 53b are delay line devices such as the embodiment illustrated in FIG. 1. The outputs from the two sensor elements 53a and 53b are conducted through feed-through leads 57a and 57b, respectively, and compared in a circuit 58. The circuit 58 includes a frequency mixer and a frequency counter that measures the difference between the oscillation frequencies of the active device 52 and the reference device 51. The circuit 58 is also provides on output 59 of this frequency difference for any auxiliary equipment. As both devices are affected equally by temperature changes, only the different responses to pressure affects the difference frequency from circuit 58.

The sensor embodiment illustrated schematically in FIG. 8 avoids problems with slowly-varying frequency changes such as those caused by ambient temperature changes. The sensor includes a sensor element 61 which may be of the type illustrated in FIG. 1. However, interposed between the sensor element 61 and the frequency counter 62 is a phase-locked loop circuit 63, and a high-pass filter 66. One possible embodiment of the high-pass filter 66 is an RC filter comprising a capacitor 64 and a resistor 65. Slow changes in the phase-locked loop 63 output, caused by its input signal drifting with temperature, are blocked by the filter 66, so that the signal to the frequency counter 62 is temperature compensated. Other slowly-varying conditions are also compensated for.

Other solutions to the problem of providing selective response include packaging to exclude unwanted influences, exploiting solubility parameter matching or selective chemical reactions in chemical sensors, employing thermal desorption spectroscopy in vapor or gas sensors, using selective immunological reactions in biosensors, and pattern recognition to obtain a definitive indication from an array of sensors that are only partially selective.

A passive delay line embodiment of the Lamb-wave sensor pursuant to the invention is illustrated in FIG. 9. In this embodiment, a delay line is used having launching and receiving transducers, 71 and 72 respectively, separated on a propagation medium 70 capable of supporting Lamb waves, similar to the embodiment shown in FIG. 1. A variable- frequency voltage source 73 activates the launching transducer 71 and also supplies a reference voltage signal $V_R$ to an amplitude and phase comparitor 74, which may be a vector voltmeter, a network analyzer, or an instrument that measures time delay and signal magnitudes. Lamb waves activating the receiving transducer 72 cause an electrical output $V_A$ that is also supplied to the comparitor 74. The characteristics of the propagation medium, and hence the measurands, which affect the medium, can be determined from the comparitor outputs 75 and 76.

An alternative embodiment 80 of the invention is illustrated in FIG. 10 and instead of a delay line employs a one-port device 81 operated as a passive element. A launching transducer 84 is activated by a variable frequency voltage source 85, through a measuring circuit 86. The launching transducer 84 is coupled to the propagation medium 87, having a ground plane 88 connected to ground. The circuit 86 measures the current and voltage supplied to the transducer 84, while the frequency varies in a known fashion. The variations of the transducer current and voltage with frequency of the voltage source, are sensitively affected by the characteristics of the propagation medium 87. Therefore, measurand values affecting the propagation medium can be determined from the variations of transducer voltage and current.

Figure 11:
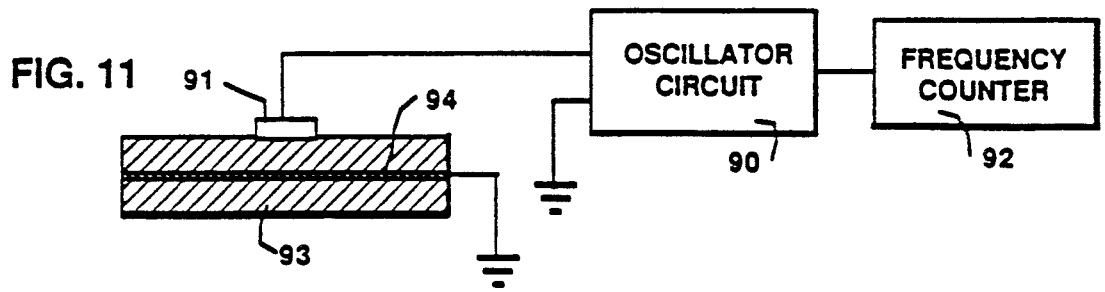
FIG. 11 is a schematic cross-sectional view of an active one-port form of the sensor of this invention.

In the active one-port embodiment shown in FIG. 11, the transducer 91 is coupled to the propagation medium 93 having a ground plane 94 connected to ground. The transducer 91 is electrically connected to an oscillator circuit 90. Characteristics of the propagation medium 93 determined by a measurand, affect the electrical input impedance of the transducer 91, and thus affect the oscillator frequency measured by the frequency counter 92. Therefore, the value of the measurand can be calculated from the measured frequency.

Figure 12:
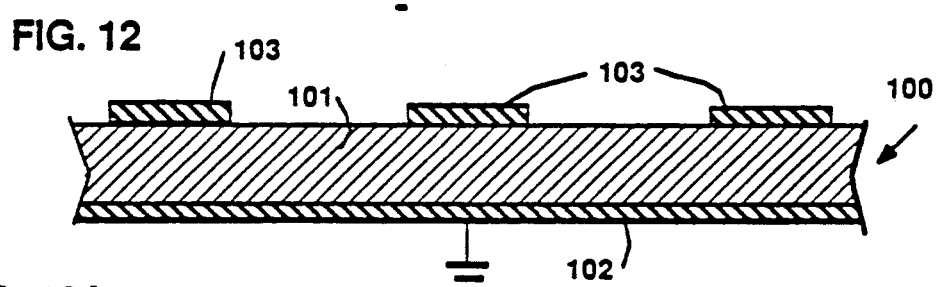
FIG. 12 is an enlarged schematic view of another transducer arrangement which may be used pursuant to the invention, where the membrane is nonconducting and nonpiezoelectric.

An alternative form of the propagation medium 100 and transducer 103 is illustrated in FIG. 12. In this embodiment no piezoelectric material is required to induce deformation of the propagation medium 100 to launch the Lamb waves. Rather, the transducer electrodes 103 are capable of creating an electrical field above the ground plane 102 of sufficient intensity to deform the non-piezoelectric and nonconducting material 101, which is included in the propagation medium or membrane 100. This non-piezoelectric propagation medium 100 may be used in a passive one-port sensor, where no signal need be received from the propagation medium.

Figure 12A:
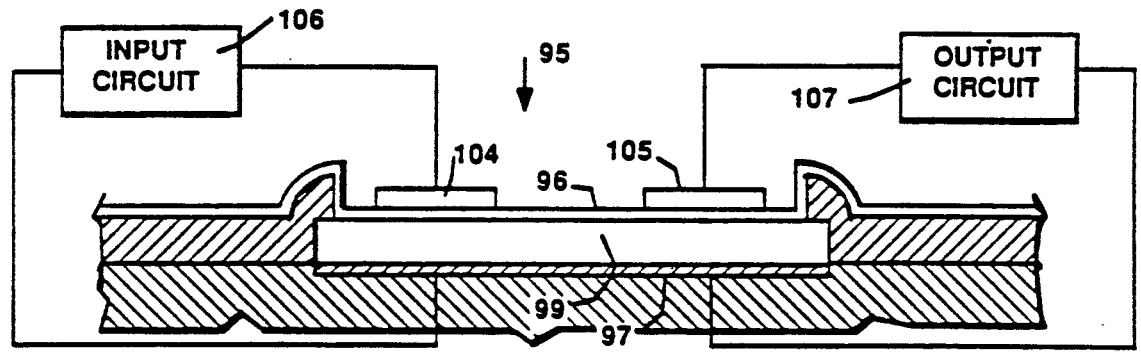
FIG. 12A is another embodiment employing a nonpiezoelectric material for the membrane.

FIG. 12A shows another arrangement for a sensor 95, including a propagation medium 96, with a launching transducer 104 and a receiving transducer 105. The propagation medium 96 is separated from a conducting plane 97 by an evacuated, gas filled, or liquid filled gap 99. The input circuit 106 in this form may be a voltage source to generate waves, a network analyzer to measure impedance, or an oscillator circuit. The output circuit 107, which is needed only for the illustrate two-port embodiment, is a measuring means for detecting the wave capacitivity, such as the voltage source and resistor arrangement discussed in connection with FIG. 13.

Figure 13:
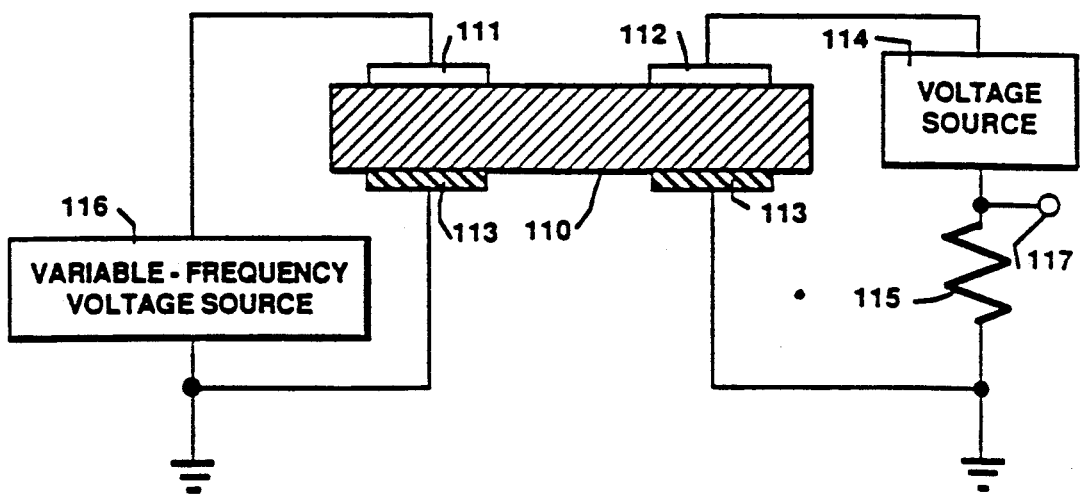
FIG. 13 is a schematic cross-sectional representation of a nonpiezoelectric-membrane delay line.

A delay line structure using a non-piezoelectric and nonconducting propagation medium 110 is illustrated in FIG. 13. The delay line includes a launching transducer 111 and a receiving transducer 112 on one surface of the propagation medium 110. A ground layer 113 is located on the surface of the propagation medium, opposite the transducer 111 and the transducer 112. A variable-frequency voltage source 116 is connected to the launching transducer The receiving transducer 112 is connected to a d.c. voltage source 114 and an output resistor 115, which is connected in series.

In operation, as the Lamb waves pass under the receiving transducer 112, the capacitance between the transducer electrodes and the ground plane changes due to the varying distance between the two. As the capacitance changes, the d.c. voltage source 114 will cause an a.c. current to flow through the resistor 115, producing an output voltage signal at the output 117. This signal is representative of the Lamb wave passing under the receiving transducer 112.

The frequency of the Lamb waves produced at the transducer 112 is actually twice the frequency of the signal supplied by the variable-frequency voltage source 116. The frequency of the output voltage at output 117 equals the Lamb wave frequency, or twice the frequency of the voltage source 116. Thus, where the non-piezoelectric delay line is used in a feedback oscillator form, the signal fed back to the launching transducer must be divided, either before or after amplification, by a frequency divider that divides the signal frequency in half.

For Lamb waves in antisymmetric modes, an asymmetrical structure between the transducers and the ground plane with respect to a median plane in the propagation medium, may be used. Another form for antisymmetric Lamb wave modes is a transducer electrode structure on either side of the propagation medium, staggered with respect to each other in the direction of wave propagation.

Figure 14:
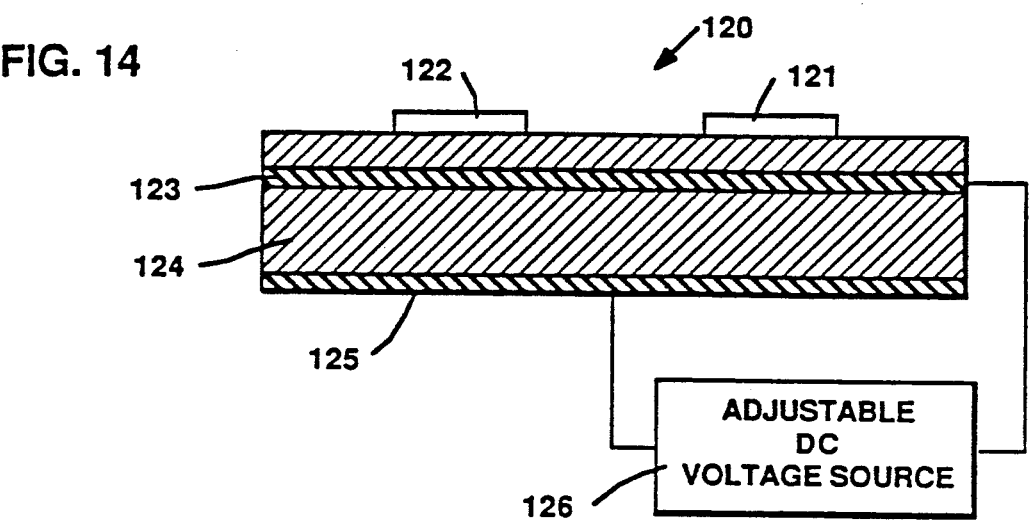
FIG. 14 is a schematic representation of a delay line sensor embodying the principles of the invention having an adjustable membrane stiffness.

In the embodiment illustrated in FIG. 14, The propagation medium 120 includes an electrode layer 125 on its surface opposite the launching transducer 121 and the receiving transducer 122. The propagation medium 120 also includes a ground plane 123 and an adjustable d.c. voltage supply 126 for producing a potential between the electrode and ground plane, across a layer 124 of nonconducting material.

The deformation of the nonconducting layer 124 due to the applied voltage from the voltage source 126 alters the elastic stiffness of the layer 124, thereby affecting the propagation velocity of the Lamb waves along the propagation medium 120. This velocity effect may be used to measure the potential applied between the ground plane 123 and the electrode 125, and it may also be used to permit adjustment of the Lamb wave velocity in the device. By adjusting the wave velocity along the propagation medium 120, the sensor may be adjusted to a desired value at the start of a measurement, of a desired measurand. Although a layered membrane or medium is illustrated the adjusting electrode 125 could be used in a non-piezoelectric device such as the one illustrated in FIG. 13.

Figure 15:
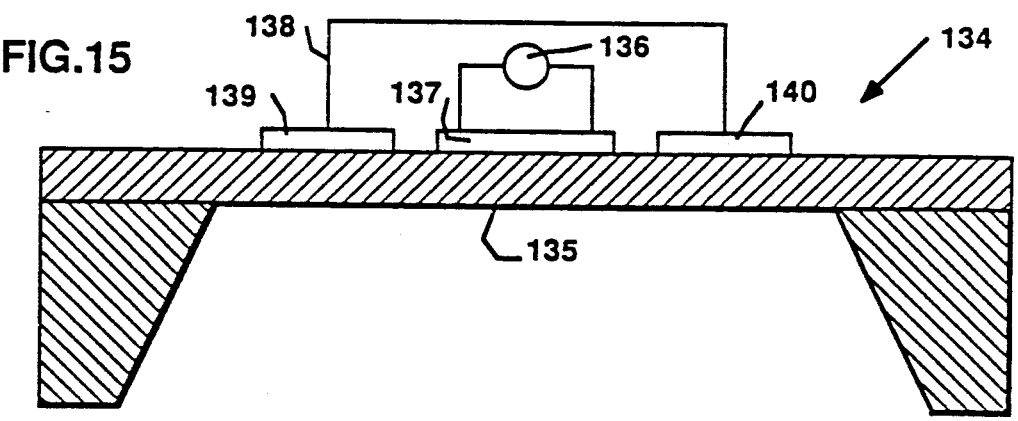
FIG. 15 is a schematic view of another form of the invention using integral acoustic amplification.

Another form of the Lamb-wave sensor 134, using integral acoustic amplification, is illustrated in FIG. 15. In this embodiment a delay line is formed similarly to the structure shown in FIGS. 1 and 6. However, the piezoelectric material forming a layer (not shown) of the membrane 135 is also a semiconductor. A voltage source 136 is applied to an electrode 137 that extends along the propagation medium 135. It has been shown that such a voltage source along a piezoelectric semiconductor carrying a wave form can provide amplification to the wave form. Thus, the amplification necessary for oscillation is applied integrally in the propagation medium or membrane 135, eliminating the need for an amplifier in the feedback path 138 between the transducers 139 and 140. As an alternative to the single layer of piezoelectric semiconductor material discussed above, integral acoustic amplification may also be achieved using a membrane including a thin layer of semiconductor material and a separate thin layer of piezoelectric material. The two-layer embodiment avoids the material quality trade-offs involved with using a single material having both piezoelectric and semiconductor properties.

Figure 16:
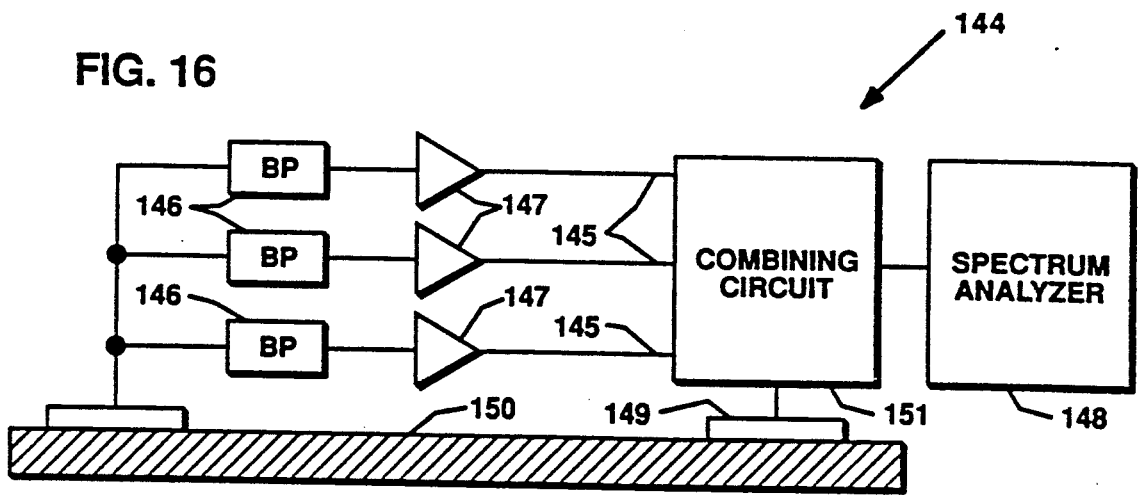
FIG. 16 is a schematic view of a Lamb-wave sensor according to the invention, utilizing multiple-frequency oscillation.

FIG. 16 illustrates an embodiment of the invention that provides multiple frequency oscillation. A device 144 includes a combining circuit 151, a frequency determining circuit 148, and a plurality of feedback paths 145, each having a bandpass filter 146, and an amplifier 147. The signal from each feedback amplifier 147 is combined by the combining circuit 151 and fed back to a launching transducer 149, which generates Lamb waves in a propagation medium or membrane 150. The frequency determining circuit 148 may be a spectrum analyzer, for example. Alternatively the frequency determining circuit may include a frequency counter and an adjustable filter means for passing a desired frequency. In either of these embodiments only one measuring circuit is used although a plurality of frequency bands may be operating simultaneously through the plurality of feedback paths.

Figure 17:
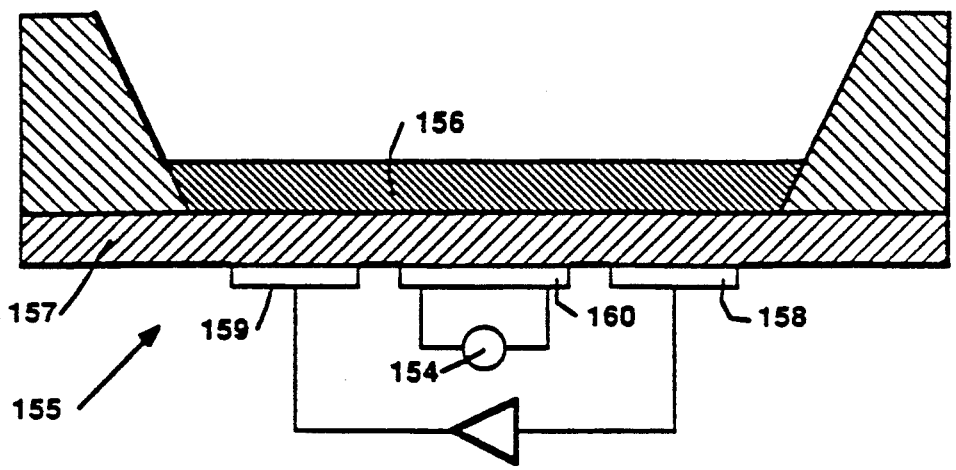
FIG. 17 is a schematic cross-sectional view of a sensor according to the invention for performing thermal desorption spectroscopy.

The Lamb-wave sensor illustrated in FIG. 17 is equipped for thermal desorption spectroscopy. This embodiment is feasible with the present sensor, due to the thinness of a propagation medium 155, which allows rapid heating of a sorptive layer 156. In this embodiment, the layer 156 of sorptive material is deposited on one surface of a base propagation medium or membrane 157 and forms part of the propagation medium. Transducers 158 and 159 are located on the opposite surface Also, on the opposite surface is located a heating element 160, powered by power source 154, which enables rapid controlled heating of the sorptive layer 156.

When the sorptive material 156 is exposed to certain vapors or gases, the vapors or gases will be sorbed at the surface or in the interior of the sorptive layer. As the temperature of the membrane 157 and sorptive layer 156 increases, the sorbed molecules will leave the sorptive material at certain temperatures depending upon the particular sorbed molecules, causing the mass loading and possibly other characteristics of the propagation medium or membrane 157 to change. Thus, by correlating such measured mass changes with the temperatures of their occurrence, the composition of the sorbed vapors or gases may be determined. Further, the device may be used as a tool to study the thermal desorption characteristics of sorptive materials deposited on it.

Where a sorptive layer is deposited on a sensor membrane according to this invention, the surface area of the membrane, and thus the sorptive material, may be increased by making the membrane porous. The sorptive material adheres to the pore walls to provide a greater surface area. A membrane according to this invention may be made porous by particle track etching either completely through its thickness to provide porosity and permeability, or through only a portion of its thickness to provide only porosity. Other sensor membrane embodiments may also be made porous, or both porous and permeable, by particle track etching.

For reasons of economy, the addition of sorptive coatings should be done at wafer scale when semiconductor microfabrication techniques are employed in fabricating the sensors. However, membranes having different sorptive films may be desired in a single wafer. Such different sorptive materials may be deposited by repetitive photomasking, or preferably, with an ink-jet printing process. In the preferred case, an ink-jet printing head having multiple jets may have each jet independently supplied with a different sorptive material, usually a polymeric liquid. The ink-jet head, translated near and in a parallel plane with the wafer, may deposit controlled amounts of material in well defined locations. Thus, different sorptive materials may be deposited on membranes made from a single wafer or substrate material.

Figure 18:
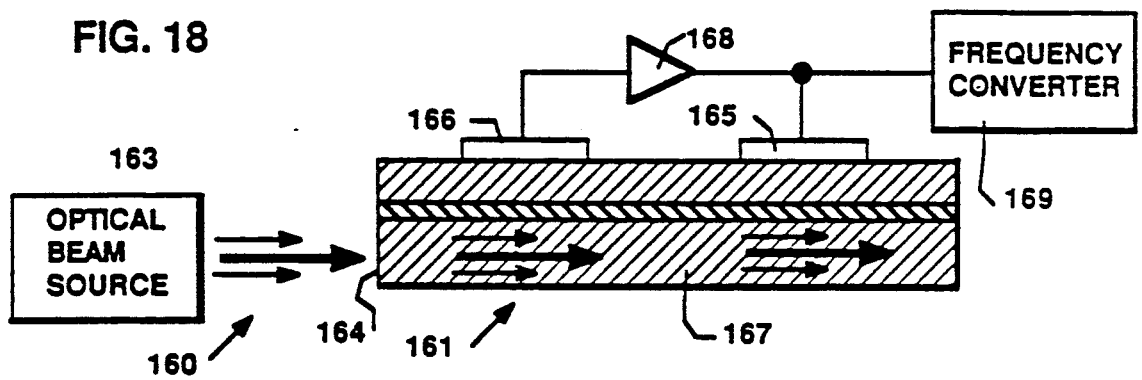
FIG. 18 is a schematic cross-sectional view of a sensor according to the invention for performing photothermal desorption spectroscopy.

The sensor illustrated in FIG. 18 may be utilized for photothermal, photoacoustic, and optical desorption spectroscopy. This form of the sensor incorporates an optical beam 160 that can interact with substances (not shown) contacting, or near the surface of, the membrane 161, which includes a layer of transparent material 167. The substance contacting the membrane 161 may be a fluid in which the membrane is immersed, a material deposited on the membrane, or molecules sorbed in a sorptive layer on the membrane, for example. The optical beam 160 is directed from a beam source 163 through a free unsupported end 164 of the membrane 161. The beam 160 passes through the layer of transparent material 167, which may be silicon nitride, for example. The illustrated membrane also includes a launching transducer 165, a receiving transducer 166, a feedback amplifier 168, and a frequency counter 169, similarly to the embodiment shown in FIG. 1. Although the delay line structure is shown, a one-port embodiment of the sensor, such as those illustrated in FIGS. 10 and 11, could also be utilized.

The optical beam 160 propagates within the transparent material layer 167 in the membrane 161 and produces evanescent electromagnetic fields at the optical frequency, in the close vicinity just outside the membrane. At certain frequencies, processes can occur in the substance contacting or near the membrane, and the processes can affect the membrane or propagation medium to produce a sensor output. These outputs, obtained as a function of optical frequency, can help identify the substances near or contacting the membrane surface.

Figure 19:
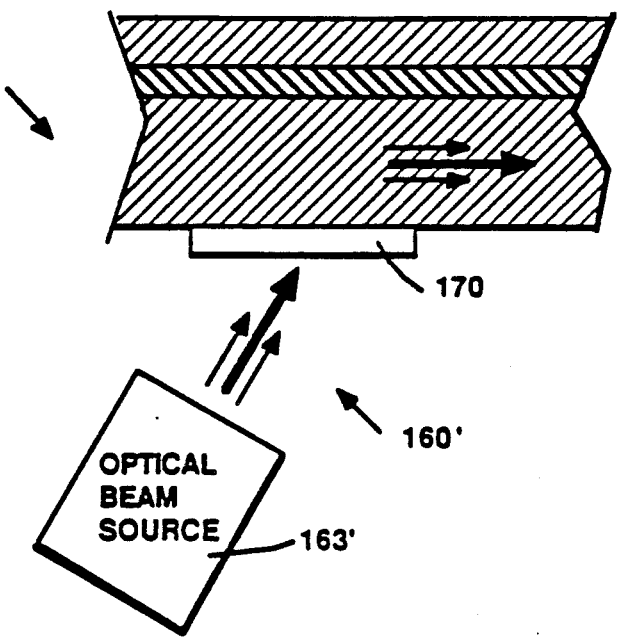
FIG. 19 is a schematic cross-sectional view an alternative device for introducing an optical beam into the membrane.

FIG. 19 shows an alternative embodiment for introducing an optical beam 160' into a transparent layer 167'. In this form the optical beam 160' is produced by a beam source 163' and introduced through an optical diffraction grating 170' formed on a membrane 161'. The beam 160' may exit the membrane 161' through a similar grating (not shown).

Also, in some embodiments it may be preferable to direct the optical beam through the membrane at an angle to the plane of the Lamb wave propagation medium, rather than through a layer of the medium as illustrated.

Figure 20:
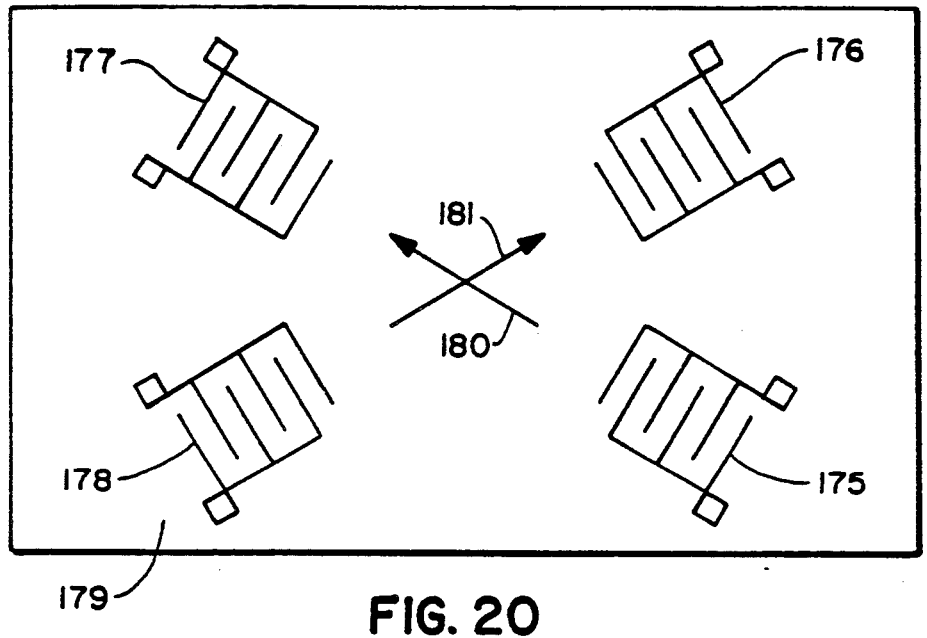
FIG. 20 is a schematic plan view of a Lamb-wave sensor using multiple direction propagation.

FIG. 20 illustrates a sensor, pursuant to the invention having two sets of transducers for multi-directional Lamb wave propagation. The device includes launching transducers 175 and 176 and receiving transducers 177 and 178 coupled to a propagation medium 179. The wave paths illustrated by arrows 180 and 181 may be oriented at any angle to each other, the respective Lamb waves propagating independently of each other. The wavelengths of the waves in each path may be different, for example, by using transducer pairs having different periods as illustrated. Use of this design makes it possible to increase the amount of sensory data obtainable from a membrane. Although delay line structures are shown, multiple one-part devices on a common propagation medium could be used.

Figure 21:
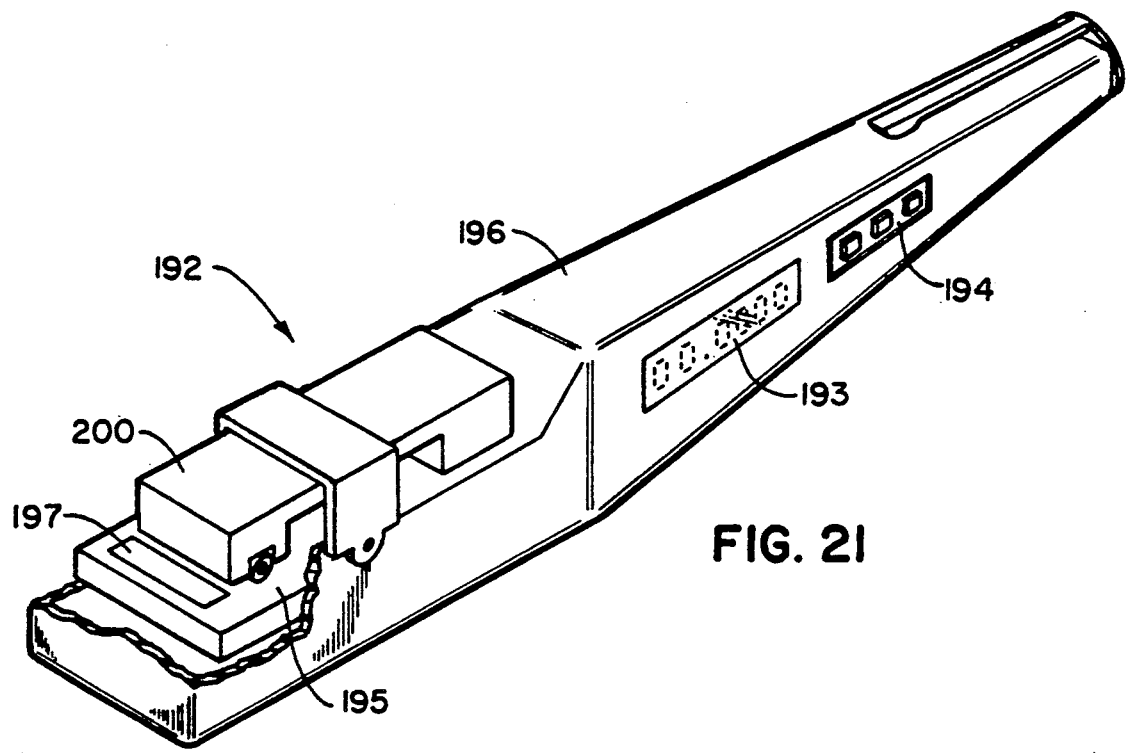
FIG. 21 is a view in perspective of a hand-held Lamb-wave sensor according to the invention.

The fabrication techniques available for producing the propagation medium or membranes used in the invention make feasible sensors that include disposable membranes operated in a reusable holder that supports and connects electrically to the disposable membranes. FIG. 21 shows a sensor 192 in which a propagation medium or membrane 197 is included on a disposable sensor chip 195. The chip 195 is received in a holder 196, which includes all of the auxiliary equipment, such as the feedback amplifier and frequency counter (not shown). The holder 196 may also include a display 193 for providing a sensor readout and controls 194. The hand-held sensor 192 may be used for biological testing, for example, in which the membranes 197 become contaminated or are damaged. The chip containing the contaminated or damaged membranes 197 may be detached and discarded, while the auxiliary equipment in the holder 196 may be used with a new chip.

Figure 22:
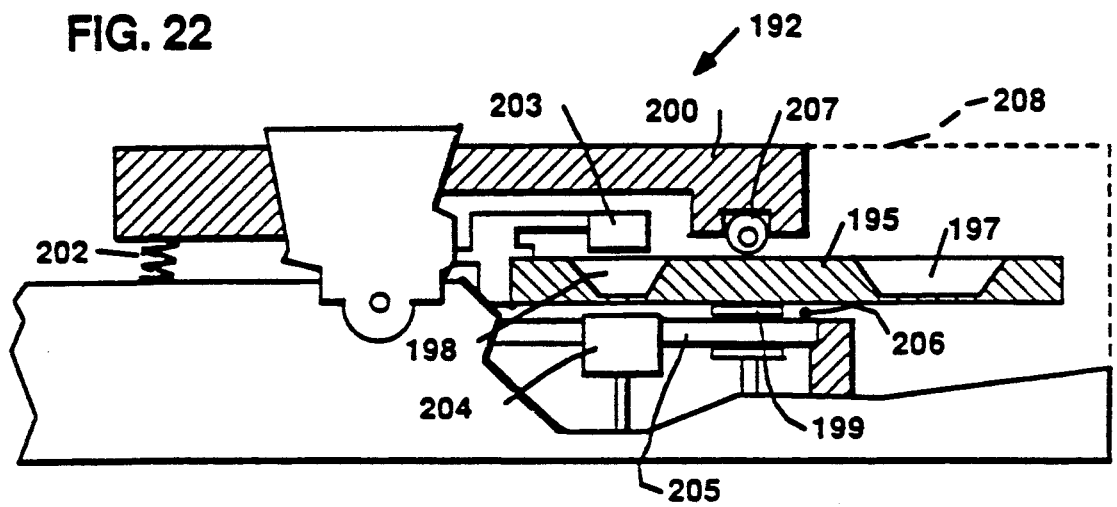
FIG. 22 is a partial sectional view of a membrane holding structure for a hand-held Lamb-wave sensor embodying the principles of the invention.

As shown in FIG. 22, the hand-held sensor 192 may include a printed circuit board 205 having conducting pressure pads 199 that physically contact thin-film electrodes (not shown) on the sensor chip 195 to make connection to the transducers directly or to integrated circuitry made on the chip. Means for supporting and firmly holding the chip 195 in a way that minimizes bending or other distortion of the membrane may include a clamp member 200 biased against the chip with biasing spring 202. The supporting means also includes vapor and liquid seals 206 and 207 that also help clamp the sensor chip. A removable cover 208 protects the chip 195 and the holder 196 when not in use. An optional optical readout means including a lamp 203, and a photodetector 204 may be included for reading identification and calibration information marked on the transparent film 198 on the chip 195. Circuitry (not shown) for controlling the measurement of frequencies and their interpretation, and means for signal transmission from the holder to external data-handling equipment may also be included in the holder 196. For certain chemical and biological testing where the membranes on a disposable chip are coated with material which may be impaired by prolonged contact with the atmosphere, new chips may be packaged individually in inexpensive plastic or foil containers until their use.

The detachable sensor chip also allows set-up chips containing specialized circuitry to be inserted into the fixture to test the holder's electrical components periodically.

Figure 23:
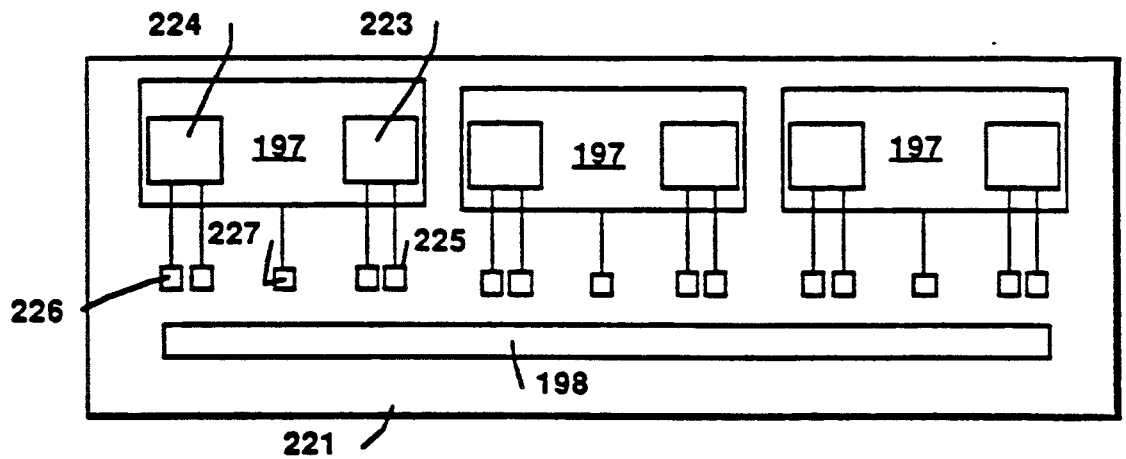
FIG. 23 is a somewhat schematic top plan view of a disposable sensor chip according to the invention.

FIG. 23 illustrates a sensor chip 195 including a substrate 221 holding three propagation media or membranes 197. Each membrane includes two transducer structures 223 and 224, each transducer also having separate contact pad sets 225 and 226 formed on the chip 195. The membranes 197 may be of the type which includes a ground plane (not shown), in which case ground contact pads 227 will also be formed on the chip. A transparent film 198 may also be formed in the chip 195 and encoded with marks (not shown) representing information identifying the particular chip and also calibration data for the particular chip, such as frequencies of zeroth-order antisymmetrical and symmetrical mode oscillations under reference conditions. The transparent film 198 may be a layer of silicon nitride, for example. The information marked on the transparent film 198 may be in the form of openings (not shown) in an opaque film, such as aluminum, which is deposited on the transparent film. The on-chip calibration data economically conveys calibration information such that the information is electronically accessible to the measurement system. Alternatively, the on-chip information may be in the form of bits stored in an on-chip memory that is read out electronically.

Figure 24:
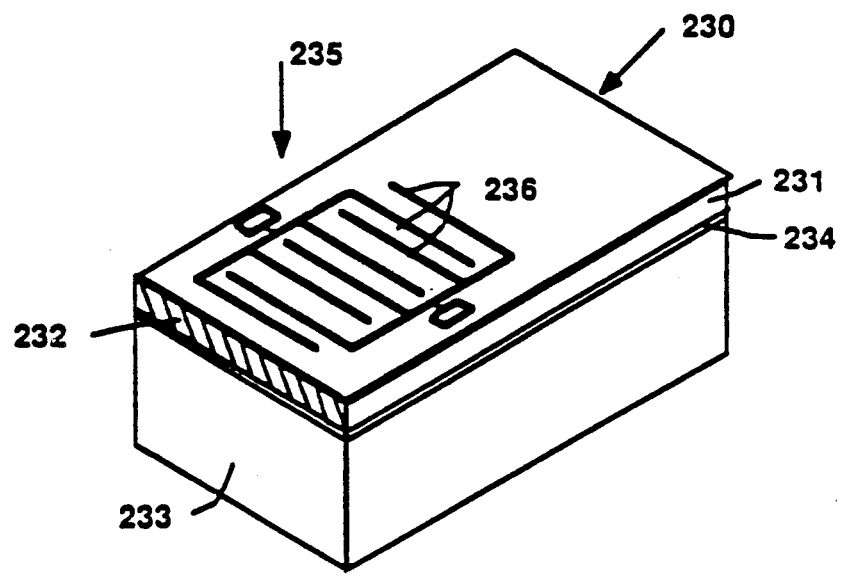
FIG. 24 is a mostly schematic view in perspective and drawn to exaggerated vertical scale, illustrating a Lamb-wave sensor device according to the invention that can accommodate shear horizontal Lamb wave propagation.

In FIG. 24, the propagation medium 230 is configured so that horizontally-polarized shear Lamb waves are propagated along the medium. The shear waves are launched by the launching transducer 235 in a piezoelectric layer 231 deposited so that its hexagonal crystal axes 232 make an acute angle to the silicon nitride layer 233 and ground plane 234. The deposition technique by which the piezoelectric layer is deposited involves properly tilting the plate relative to the material source during the sputtering process. The effect of the tilting is to cause the piezoelectric film to deform only in the transverse direction, parallel to the electrode fingers 236, when a voltage is applied to the transducer 235. This deformation produces a propagating "shear-horizontal" Lamb wave having a particle motion only in the transverse direction and perpendicular to the direction of propagation. At a receiving transducer (not shown) similarly situated on the membrane, the shear-horizontal wave produces a corresponding electrical output voltage. Shear horizontal Lamb waves are particularly sensitive to viscosity of a fluid loading the propagation medium. Thus, propagation medium 230 is particularly useful in a viscosity sensor.

Figure 25:
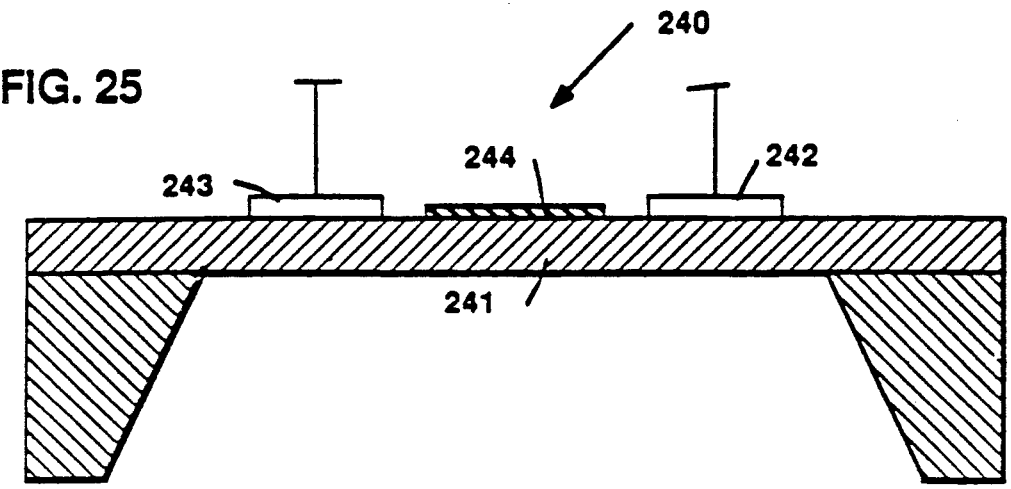
FIG. 25 is a schematic cross-sectional view of a magnetic field sensor according to the invention.

FIG. 25 shows a sensor 240 for sensing magnetic fields. The delay line structure similar to that shown in FIG. 1 is used, having a launching transducer 242 and a receiving transducer 243, both coupled to a propagation medium or membrane 241. However, in this embodiment, the propagation medium 241 has deposited on it a magnetic material 244, which may be a film of permalloy, for example. When a magnetic field is present, the force exerted by the field on the magnetic material will deflect the membrane, affecting the membrane's Lamb wave propagation characteristics. These changed propagation characteristics can be detected as in previous embodiments.

Figure 26:
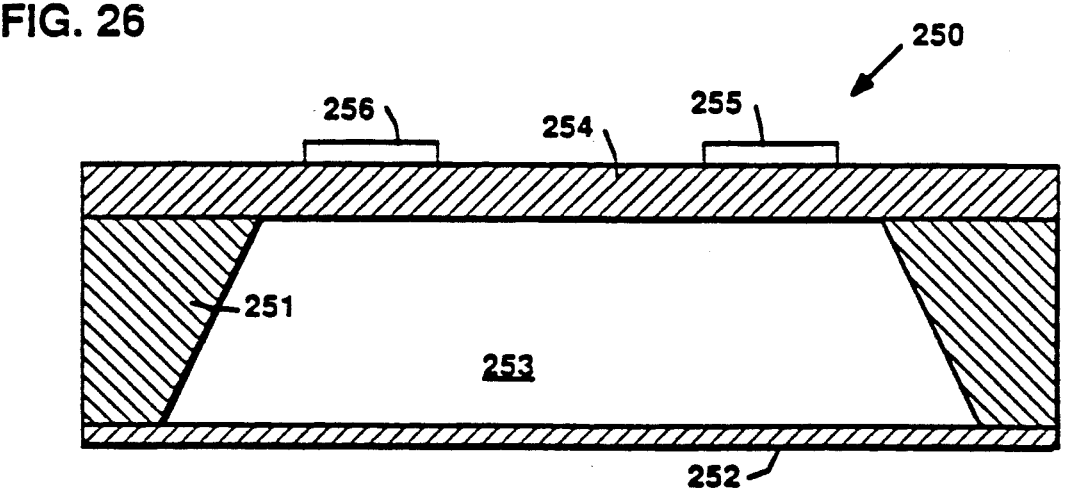
FIG. 26 is a schematic cross-sectional view of a sensor according to the invention equipped with a filtering medium.

With biosensors and chemical sensors, it is helpful, and in some cases necessary, to reduce the number of types of molecules that can reach the propagation medium or membrane. A sensor 250, illustrated in FIG. 26, includes a filtering film 252 positioned across an opening 253 in a substrate material 251. The filtering film or medium 252 may be, for example, a plastic dialysis membrane. The illustrated sensor includes a delay line structure similar to that described in connection with FIG. 1. The delay line includes a propagation medium 254, and transducers 255 and 256.

Figure 27:
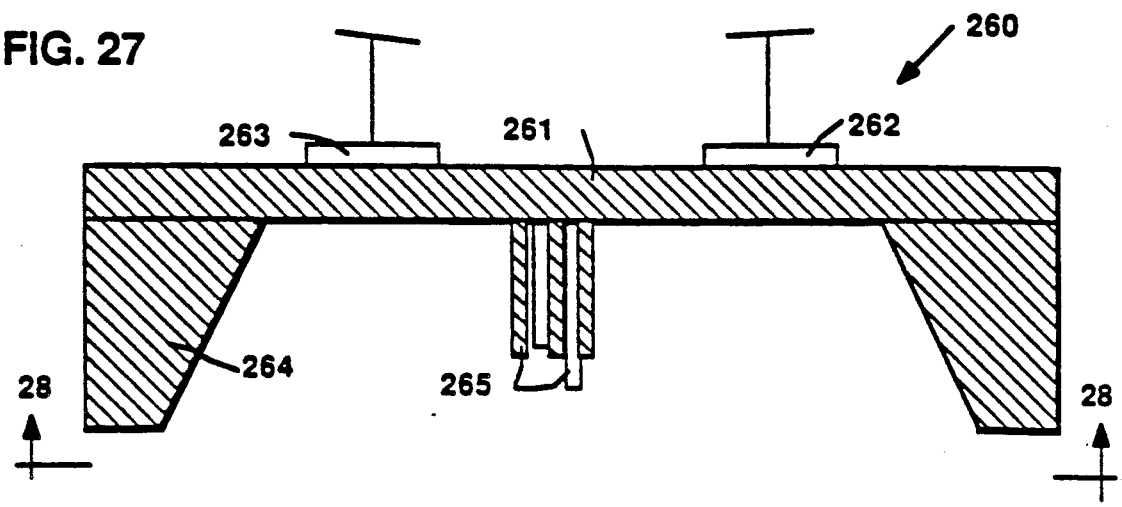
FIG. 27 is a schematic cross-sectional view of an accelerometer according to the invention.
Figure 28:
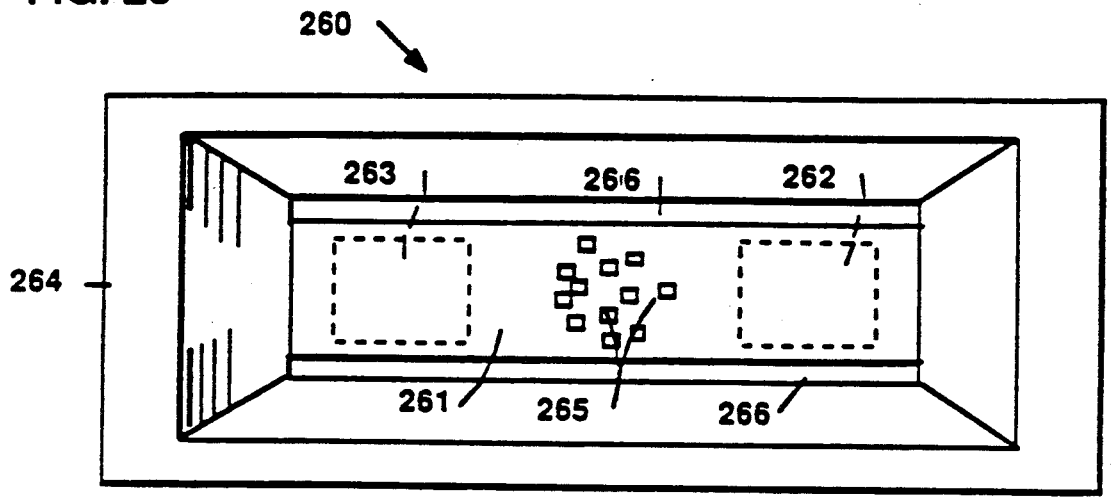
FIG. 28 is a schematic bottom plan view of the accelerometer shown in FIG. 27.

FIGS. 27 and 28 show a sensor 260 according to the invention for sensing acceleration. The delay line structure is again illustrated, having a propagation medium or membrane 261, transducers 262 and 263, and a substrate 264. A number of proof masses 265 are attached to the membrane to generate a greater force for a given acceleration in a direction perpendicular to the plane of the membrane. As shown in FIG. 28, the membrane 261 is not attached to the substrate 264 along the side areas 266, giving the membrane greater freedom to respond. The proof masses 265 are randomly located, to avoid cooperative interference effects, and of random length. The masses are also concentrated near the center of the membrane 261 for maximum membrane response. The cross-sectional dimension of the proof masses 265 as shown in FIG. 28, should be small compared with Lamb-wave wavelength. Where the sensor is formed from a silicon wafer, the proof masses 265 may preferably be remnants of the silicon wafer left attached to the membrane.

Figure 29:
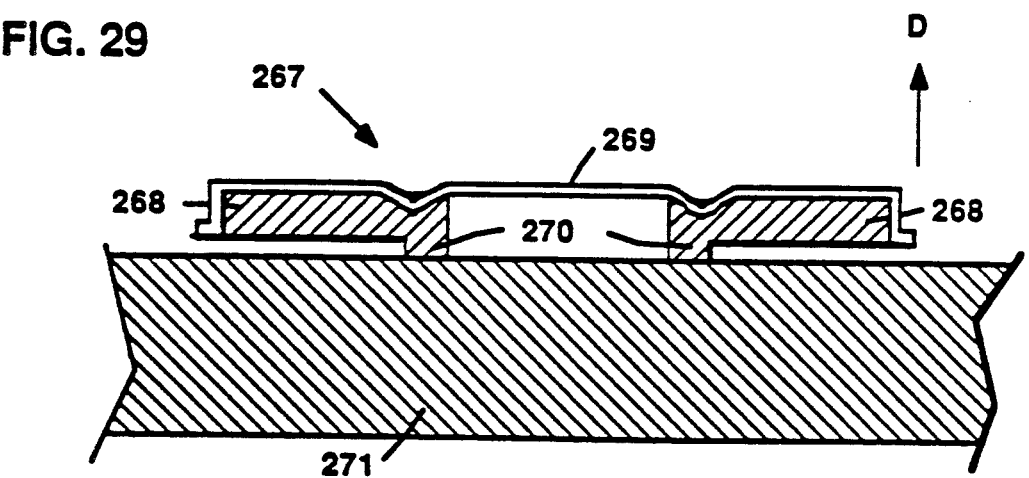
FIG. 29 is a schematic cross-sectional view, drawn to an exaggerated vertical scale, of an alternative accelerometer according to the invention.

In an alternative accelerometer 267 shown in FIG. 29, proof masses 268 are located at the ends of a membrane 269. As this embodiment is accelerated in the direction indicated by arrow D, for example, the proof masses 268 are forced in the opposite direction and pivot slightly about substrate extensions 270 extending above a substrate 271. The movement of the proof masses 268 varies the stress in the membrane 269 indicating the acceleration magnitude.

Figure 30:
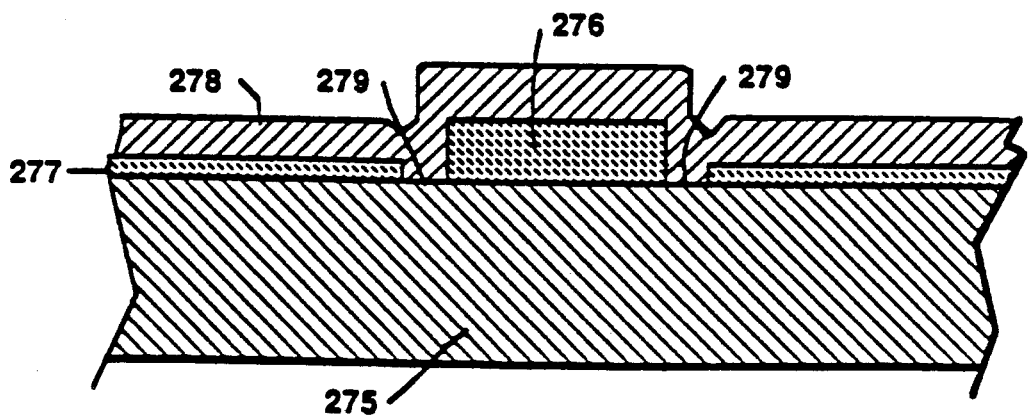
FIGS. 30-34 are schematic cross-sectional views, drawn to an exaggerated vertical scales, showing intermediate forms taken in the production of the accelerometer illustrated in FIG. 29.

As illustrated in FIGS. 30-34, the embodiment shown in FIG. 29 may preferably be produced using semiconductor microfabrication techniques as in the other sensor forms. As shown in FIG. 30, a central layer 276 and outer layers 277 of silicon dioxide are first grown or deposited on a thick silicon substrate 275. A layer 278 of poly-silicon is formed over the layers 276 and 277 of silicon dioxide and the exposed silicon areas 279 between the layers of silicon dioxide. Although layers 276 and 277 of silicon dioxide are shown as having different thicknesses, they could all be of the same thickness.

Figure 31:
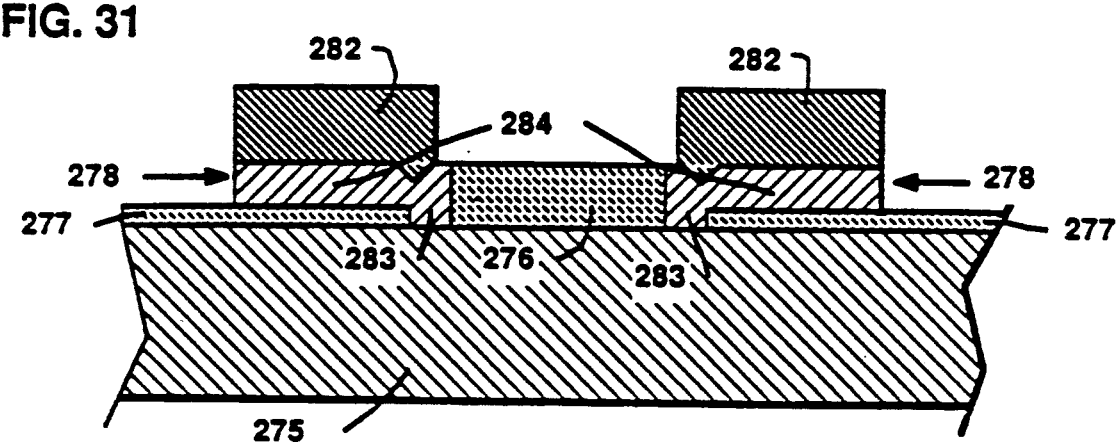

As shown in FIG. 31 the poly-silicon 278 is covered with photoresist 282 and plasma etched to form the substrate extensions 283 and proof masses 284, corresponding to those shown in FIG. 29.

Figure 32:
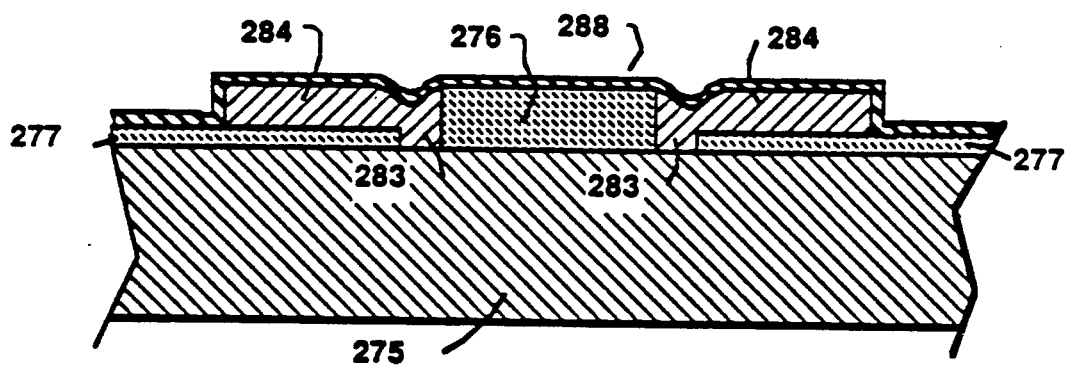
Figure 33:
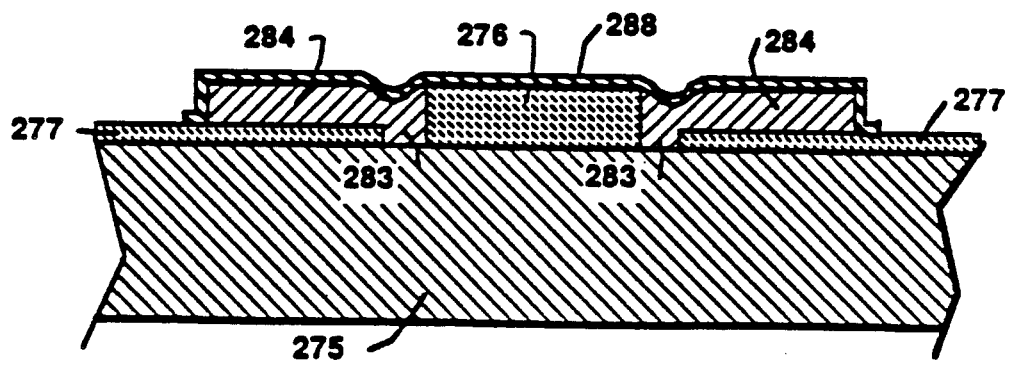

FIG. 32 shows the photoresist removed and a LPCVD silicon nitride layer 288 formed over the extensions 283 and the proof masses 284, as well as the silicon dioxide layers 276 and 277. The silicon nitride layer 288 is then masked with photoresist and etched by plasma etching to form the structure shown in FIG. 33.

Figure 34:
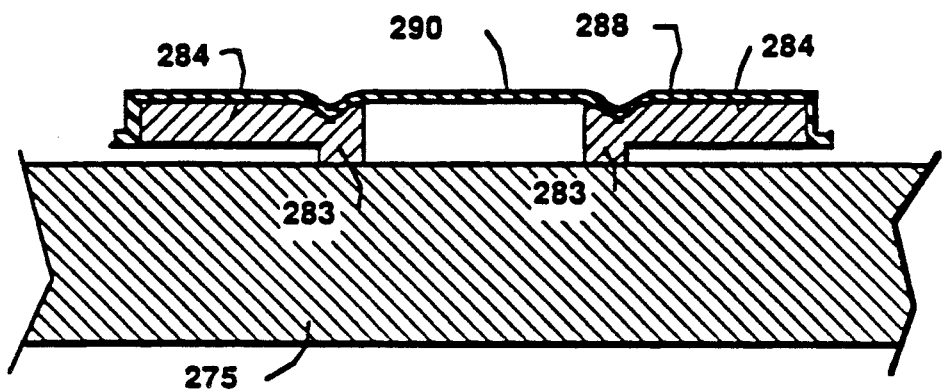

As illustrated in FIG. 34, the silicon dioxide layers 276 and 277 are then etched away leaving the proof masses 284 and the substrate extentions 283 covered with silicon nitride layer 288. The silicon nitride portion 290 suspended between the proof masses 284 and the extenions 283, forms the base layer of the propagation medium or membrane for the accelerometer, corresponding to the membrane shown schematically at 269 in FIG. 29.

Figure 35:
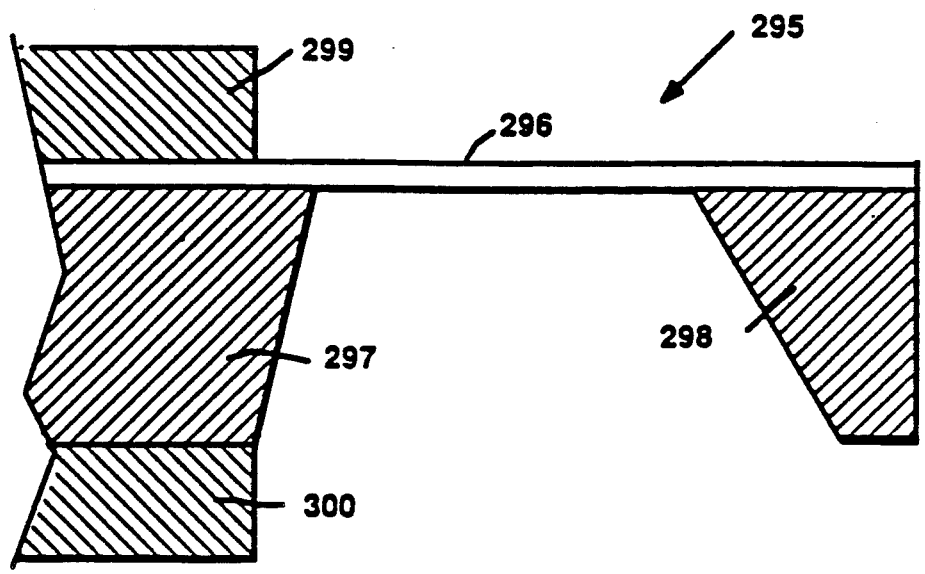
FIG. 35 is a schematic cross-sectional view of another alternative accelerometer according to the invention.

FIG. 35 illustrates another alternative accelerometer arrangement embodying the principles of the invention. The accelerometer 295 includes a propagation medium 296, formed on substrate pieces 297 and 298. The end of the sensor having substrate piece 297 is shown held in jaws 299 and 300, that are rigidly connected to the object (not shown) whose acceleration is to be measured. In this embodiment substrate piece 298 acts as a proof mass, moving relative to the other substrate piece 297 when the sensor and object to which it is fixed are accelerated in a direction perpendicular to the plane of the membrane 296. This relative movement of substrate piece 298 varies the stress in the membrane 296, and the stress is sensed as in previous sensor embodiments to indicate the acceleration magnitude.

Figure 36:
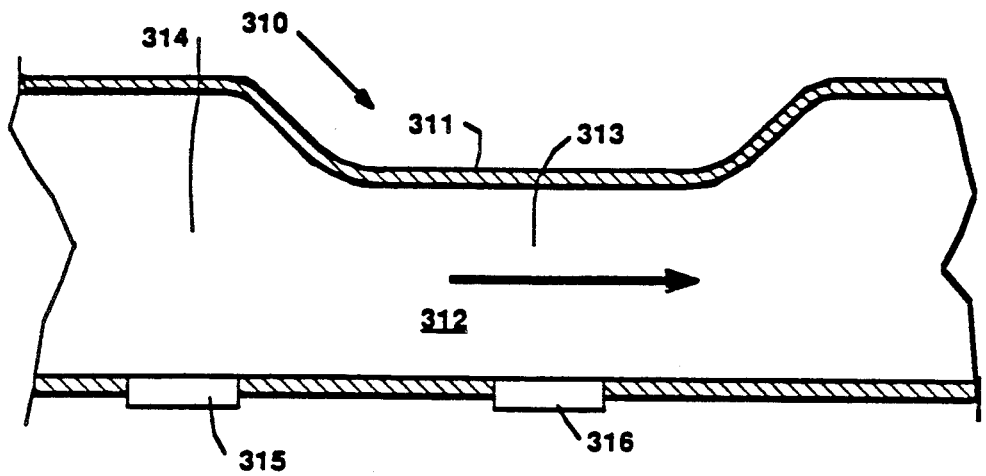
FIG. 36 is schematic sectional view of a venturi meter employing Lamb-wave sensors pursuant to the invention.

As illustrated schematically in FIG. 36, the sensor according to this invention can be employed in a venturi meter 310 to determine the flow rate of a fluid. The venturi meter 310 includes a fluid passage 311 through which a fluid 312 flows in the direction indicated by the arrow, and Lamb-wave pressure sensors 315 and 316. The fluid passage 311 includes a constricted flow portion 313 which has a lesser flow area than a flow portion 314. The sensor 315 is positioned to indicate the pressure at the flow portion 314, and the sensor 316 is positioned to indicate the pressure at the constricted portion. The pressure difference between the two sensors 315 and 316 indicates the flow rate of the fluid 312 through the fluid passage 311.

Figure 37:
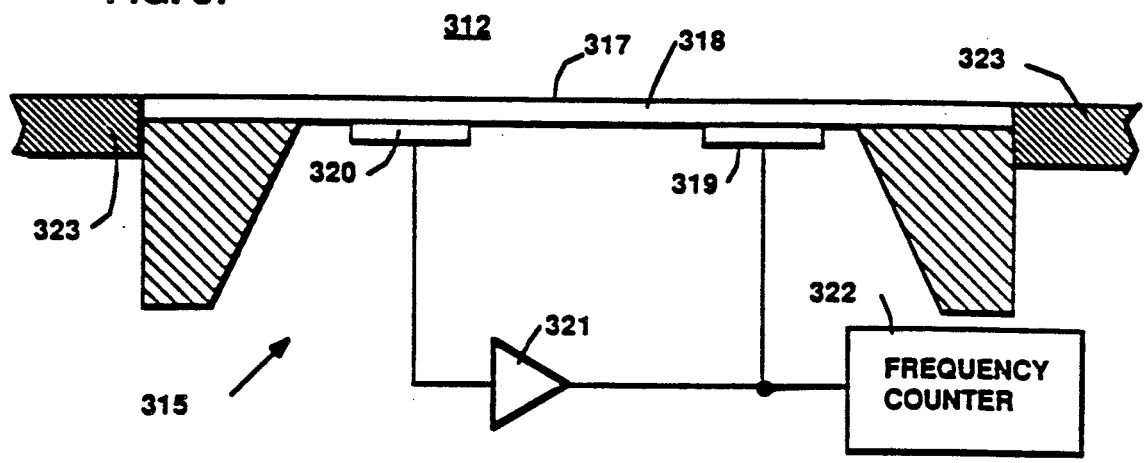
FIG. 37 is a schematic cross-sectional view showing the mounting of a Lamb-wave sensor in the fluid flow passage of FIG. 36.

The sensor 315 is mounted as illustrated in FIG. 37 with the propagation medium surface 317 substantially flush with the inner wall 323 of the fluid passage. The illustrated sensor 315 shows a delay line oscillator form with propagation medium 318, a launching transducer 319, a receiving transducer 320, a feedback amplifier 321, and a frequency counter 322. In this sensor embodiment the transducer electrodes are located outside of the fluid flow passage so that they do not contribute to turbulence in the fluid flowing through the passage. Sensor 316 is mounted similarly to the sensor 315.

The above described preferred embodiments are intended to illustrate the principles of the invention, but not to limit the scope of the invention. Various other embodiments and modifications to these preferred embodiments may be made by those skilled in the art, without departing from the scope of the following claims.

What is claimed is:

1. An ultrasonic sensor comprising:
   a composite structure comprising (a) a supporting frame of a first material and (b) a propagation medium comprising a thin planar sheet of a second, different material capable of supporting Lamb waves, supported peripherally by said supporting frame, said sheet having a thickness very much thinner than the wavelength of Lamb waves to be propagated thereon and having some physical characteristics determined by the value of a measurand acting thereon, said physical characteristics determining the propagation characteristics of Lamb waves to be propagated along the medium;
   electrical means coupled to the thin planar sheet of said propagation medium for producing Lamb waves in the propagation medium;
   output means on said sheet for producing an electrical signal representative of the determined propagation characteristics of the Lamb waves propagating along the propagation medium; and
   measuring means for measuring selected characteristics of said electrical signal,
   whereby when said sensor is acted on by a measurand, the physical characteristics of said propagation medium are determined and said electrical signal characteristics are also determined, so that said measuring means indicates the value of the measurand.

2. The sensor as recited in claim 1, wherein the electrical means includes means for producing both symmetrical and antisymmetrical Lamb waves in the propagation medium.

3. The sensor as recited in claim 2, wherein the propagation medium includes a layer of silicon nitride.

4. The sensor as recited in claim 3, wherein the propagation medium includes a layer of piezoelectric material.

5. The sensor as recited in claim 4, wherein
   the output means includes a receiving transducer, coupled to the propagation medium, for producing an electrical signal representative of the Lamb waves propagating along said propagation medium,
   the electrical means includes a launching transducer, coupled to the propagation medium, for generating Lamb waves in the propagation medium,
   a feedback path between the receiving and launching transducers for providing feedback from the receiving transducer to the launching transducer, and
   a feedback amplifier in the feedback path for amplifying said electrical signal produced by the receiving transducer and fed back to the launching transducer, the sensor forming an oscillator in which Lamb waves are continuously propagated along the propagation medium,
   the measuring means includes frequency measuring means for measuring the oscillation frequency of said oscillator formed by said sensor measuring the oscillation frequency.

6. The sensor as recited in claim 5, including Lamb wave reflecting means for reflecting Lamb waves generated by the launching transducer that propagate in directions away from the receiving transducer, so that the reflected Lamb waves do not produce an output at the receiving transducer.

7. The sensor as recited in claim 5, wherein each transducer includes a pair of interdigital finger electrodes formed on one surface of the layer of piezoelectric material.

8. The sensor as recited in claim 7, wherein the propagation medium includes a ground plane comprising a layer of conducting material on the surface of the piezoelectric layer opposite the surface on which the transducer electrodes are deposited, said ground plane being restricted to areas substantially opposite the transducer electrodes.

9. The sensor as recited in claim 7, wherein there is a ground plane that is substantially coextensive with the propagation medium.

10. The sensor as recited in claim 8, wherein the piezoelectric material is zinc oxide.

11. The sensor as recited in claim 10, wherein there is a ground plane and it and the transducer electrodes are aluminum.

12. The sensor as recited in claim 11, wherein the silicon nitride layer is about 2.0 microns thick, the aluminum ground layer and transducer electrodes are each about 0.3 microns thick, and the layer of piezoelectric zinc oxide is 0.7 microns thick.

13. The sensor as recited in claim 1, including isolator means for isolating the propagation path from direct contact with the measurand.

14. The sensor as recited in claim 13, wherein the isolator means includes a flexible enclosure, filled with an inert gas, for enclosing the propagation medium,
whereby pressure applied to the enclosure is communicated to the propagation medium directly by the inert gas.

15. The sensor as recited in claim 1, wherein the propagation medium is detachably mounted on a holder structure which contains said electrical means and said measuring means.

16. The sensor as recited in claim 15, wherein the propagation medium is supported along at least a portion of its periphery by a silicon chip which is held by said holder, the entire propagation medium and chip structure being detachable from said holder and disposable.

17. The sensor as recited in claim 1, wherein the output means includes a plurality of receiving transducers, each receiving transducer coupled to said propagation medium for producing a separate signal representative of a set of Lamb waves propagating in said propagation medium,
the electrical means including a plurality of launching transducers, each coupled to the propagation medium for producing a separate set of Lamb waves in the propagation medium to be received by a different one of the receiving transducers,
a plurality of feedback paths, each said path connecting a receiving transducer to the launching transducer which produces the Lamb waves which said receiving transducer receives, for providing feedback from said receiving transducer to said launching transducer, and
a feedback amplifier in each feedback path for amplifying the signal produced by the particular receiving transducer, the sensor forming a plurality of feedback oscillators, and wherein the measuring means includes a plurality of frequency measuring means, each for measuring the oscillation frequency of a different one of said feedback oscillators,
whereby the sensor may provide indications of several measurands simultaneously.

18. The sensor as recited in claim 1, wherein the propagation medium includes a layer having piezoelectric and semiconductor properties,
the output means including a receiving transducer coupled to the propagation medium for producing an electrical signal representative of the Lamb waves propagating along said propagation medium,
the electrical means includes a launching transducer, coupled to the propagation medium, for producing Lamb waves in the propagation medium,
a feedback path between the receiving and launching transducers for providing feedback from the receiving transducer to the launching transducer,
an electrode adjacent to and along said propagation medium, and
a voltage application means for applying a voltage to said electrode so that the Lamb waves travelling along said propagation path are amplified for feeding back to said launching transducer through the feedback path, the sensor forming an oscillator in which Lamb waves are continuously propagated along the propagation medium, and
wherein said measuring means includes frequency measuring means for measuring the oscillation frequency of said oscillator formed by said sensor.

19. The sensor as recited in claim 18, wherein the layer having piezoelectric and semiconductor properties comprises a single layer of material that exhibits both piezoelectric and semiconductive properties.

20. The sensor as recited in claim 18, wherein the layer having piezoelectric and semiconductor properties comprises two separate layers, a semiconductor layer of semiconductor material and a piezoelectric layer of piezoelectric material.

21. The sensor as recited in claim 1, wherein the propagation medium comprises a planar sheet of nonconducting and non-piezoelectric material, and
the electrical means includes electrode means for inducing a plurality of electrical fields at various positions across the nonconducting material, said fields having sufficient intensity to deform the material and thereby generate Lamb waves in the propagation medium with no need for a piezoelectric layer in the propagation medium.

22. The sensor as recited in claim 1, wherein the propagation medium includes a thin layer of black material for increasing the sensitivity of the medium to radiation.

23. The sensor as recited in claim 5, including:
an adjusting electrode on the outer surface of the propagation medium, adjacent said layer of silicon nitride; and
voltage source means for applying a voltage to the adjusting electrode,
whereby the voltage applied to the adjusting electrode alters the elastic stiffness of the medium.

24. The sensor as recited in claim 23, including a voltage varying means for varying the voltage to adjust the sensor output frequency to a desired value.

25. The sensor as recited in claim 1, wherein the electrical means includes a launching transducer for generating Lamb waves in the propagation medium, and a variable-frequency voltage source for driving the launching transducer and for producing a reference signal representative of the signal which drives the launching transducer, the output means includes a receiving transducer for producing an electrical signal representative of the Lamb waves propagating along said propagation medium, and the measuring means includes comparator means for comparing the reference signal to the signal produced by the receiving transducer and for providing outputs which indicate the value of the measurand.

26. The sensor as recited in claim 1, wherein the propagation medium includes a layer of transparent material, and including an optical beam means for generating an optical beam and for directing said beam through the transparent material, whereby the beam may interact with substances contacting or near the propagation medium.

27. The sensor as recited in claim 26, including a diffraction grating for introducing the optical beam into the transparent layer.

28. The sensor as recited in claim 26, wherein the layer of transparent material is silicon nitride.

29. The sensor as recited in claim 1, wherein at least a portion of the propagation medium is porous.

30. The sensor as recited in claim 29, wherein the porous portion of the propagation medium is also permeable.

31. The sensor as recited in claim 1, including proof mass means connected to the propagation medium for exerting a propagation characteristic changing force on the propagation medium when the sensor is accelerated in a sensing direction, whereby when the sensor is accelerated in said sensing direction, said force changes the propagation characteristics of the propagation medium so that the magnitude of the acceleration can be determined by such characteristics changes.

32. The sensor as recited in claim 31, wherein said proof mass means comprises a plurality of proof masses attached to the propagation medium at random locations near the center of the propagation medium, and wherein the sensing direction is perpendicular to the plane of the propagation medium.

33. The sensor as recited in claim 31, including pivot means for supporting said proof mass means and for allowing said proof mass means to pivot in response to acceleration in said sensing direction, and wherein the proof mass means comprises at least two proof masses each connected to the propagation medium along opposite portions of the periphery of said propagation medium, whereby said pivoting movement by said proof masses exerts said propagation characteristic changing force on the propagation medium.

34. The sensor as recited in claim 31, including support means for supporting the propagation medium at one end and for allowing said proof mass to move in response to an acceleration of the sensor in the sensing direction, and wherein the proof mass means is connected to the propagation medium at an end opposite the end which includes the support means, whereby said movement of said proof mass means in response to an acceleration in the sensing direction exerts said propagation characteristic changing force on the propagation medium.

35. The sensor as recited in claim 5, wherein the propagation medium includes along one of its outer surfaces and near the center of the propagation medium, a layer of magnetic material, whereby when the sensor is placed in a magnetic field, the layer of magnetic material exerts a force on the propagation medium, affecting the propagation characteristics thereof and allowing the intensity of the magnetic field to be determined.

36. The sensor as recited in claim 35, wherein the magnetic material is permalloy.

37. The sensor as recited in claim 4, wherein the piezoelectric material is zinc oxide and is deposited so that its hexagonal crystal axes make an acute angle to the plane of the propagation medium, whereby the electrical means produce shear horizontal Lamb waves in the propagation medium.

38. The sensor as recited in claim 21, wherein the electrode means introduces asymmetrical deformations in the propagation medium so as to generate either symmetrical or antisymmetrical Lamb waves in the propagation medium.

39. The sensor recited in claim 1, including:

a ground plane and a deformable nonconducting layer on the propagation medium, an electrode opposite the propagation medium and separated therefrom by said deformable nonconducting layer, and an adjustable voltage source having two terminals connected respectively to said electrode and to said ground plane, whereby application of the voltage causes a change in the elastic stiffness of said deformable layer, thereby affecting the propagation velocity of the elastic waves along the propagation medium and permitting adjustment of the wave velocity along the medium to a desired value.

* * * * *